US010682099B2

(12) United States Patent
Ramer et al.

(10) Patent No.: US 10,682,099 B2
(45) Date of Patent: *Jun. 16, 2020

(54) TRAINING OF AN ELECTROENCEPHALOGRAPHY BASED CONTROL SYSTEM

(71) Applicant: ABL IP HOLDING LLC, Conyers, GA (US)

(72) Inventors: David P. Ramer, Reston, VA (US); Jack C. Rains, Jr., Sarasota, FL (US); Youssef F. Baker, Arlington, VA (US); Niels G. Eegholm, Columbia, MD (US); Daniel M. Megginson, Fairfax, VA (US); Jenish S. Kastee, South Riding, VA (US)

(73) Assignee: ABL IP Holding LLC, Conyers, GA (US)

(*) Notice: Subject to any disclaimer, the term of this patent is extended or adjusted under 35 U.S.C. 154(b) by 21 days.

This patent is subject to a terminal disclaimer.

(21) Appl. No.: 15/948,448

(22) Filed: Apr. 9, 2018

(65) Prior Publication Data

US 2019/0290211 A1     Sep. 26, 2019

Related U.S. Application Data

(63) Continuation-in-part of application No. 15/934,083, filed on Mar. 23, 2018, now Pat. No. 10,551,921.

(51) Int. Cl.
*A61B 5/00* (2006.01)
*A61B 5/04* (2006.01)
(Continued)

(52) U.S. Cl.
CPC ........ *A61B 5/7267* (2013.01); *A61B 5/04004* (2013.01); *A61B 5/0476* (2013.01);
(Continued)

(58) Field of Classification Search
None
See application file for complete search history.

(56) References Cited

U.S. PATENT DOCUMENTS 6,473,639 B1 * 10/2002 Fischell ............... A61B 5/0476
600/544
8,457,705 B2 * 6/2013 Shoureshi ............ A61B 5/0059
600/323

(Continued)

OTHER PUBLICATIONS

"Nissan's 'B2V' system lets you drive a car with brain waves", https://www.nbcnews.com/mach/science/nissan-paves-way-cars-read-your-mind-ncna834811, searched Jan. 9, 2018 (4 pages).

(Continued)

*Primary Examiner* — Ramesh B Patel
(74) *Attorney, Agent, or Firm* — RatnerPrestia

(57) ABSTRACT

A system including an electroencephalography (EEG) device configured to be positioned on a head of a user and process detected EEG signals. The system also includes a processor in communication with the EEG device, a memory accessible by the processor and instructions stored in the memory for execution by the processor to generate, based on a control instruction, a control data signal, for control of an operation of a controllable device configured to provide a premises related service in an area of a premises. In the training phase, execution of the instructions configures the processor to determine whether or not that the control operation of the control data signal is consistent with the detected EEG signals based on a trusted input from the user, and upon determination that the control operation is consistent with the detected EEG signals, store, in the memory, recognition data characterizing the detected EEG signals as a predetermined set of signals in association with the control instruction.

19 Claims, 16 Drawing Sheets

(51) Int. Cl.
    *A61B 5/0476* (2006.01)
    *G06F 3/01* (2006.01)
    *G06K 9/00* (2006.01)
    *G05B 13/02* (2006.01)
    *H05B 47/105* (2020.01)

(52) U.S. Cl.
    CPC ........ *A61B 5/7221* (2013.01); *G05B 13/0265* (2013.01); *G06F 3/015* (2013.01); *G06K 9/00536* (2013.01); *H05B 47/105* (2020.01)

(56) References Cited

U.S. PATENT DOCUMENTS

| | | | |
|---|---|---|---|
| 9,449,446 B1* | 9/2016 | Mullin | G07C 9/00158 |
| 10,029,067 B2* | 7/2018 | Gerdes | A61B 5/7415 |
| 10,223,633 B2* | 3/2019 | Breuer | G06N 3/02 |
| 2014/0257073 A1* | 9/2014 | MacHon | A61B 5/6803 |
| | | | 600/383 |
| 2014/0354534 A1* | 12/2014 | Mullins | G06F 3/015 |
| | | | 345/156 |
| 2015/0282760 A1* | 10/2015 | Badower | A61B 5/04012 |
| | | | 600/383 |
| 2016/0103487 A1* | 4/2016 | Crawford | G06F 3/015 |
| | | | 600/544 |
| 2016/0143554 A1* | 5/2016 | Lim | A61B 5/6814 |
| | | | 600/383 |
| 2016/0198971 A1* | 7/2016 | Adachi | G06F 19/325 |
| | | | 600/379 |
| 2016/0360970 A1* | 12/2016 | Tzvieli | G01J 5/0265 |
| 2017/0172497 A1* | 6/2017 | Marquez Chin | G06F 19/3481 |
| 2017/0199569 A1* | 7/2017 | Cruz-Hernandez | G06F 3/016 |
| 2017/0228512 A1* | 8/2017 | Driscoll | G06F 19/3418 |
| 2018/0092557 A1* | 4/2018 | Bickford | A61B 5/0059 |
| 2018/0184974 A1* | 7/2018 | Cimenser | A61B 5/04845 |
| 2018/0285540 A1* | 10/2018 | Chen | G06F 21/32 |
| 2018/0317548 A1 | 11/2018 | Gunasekar et al. | |
| 2018/0317848 A1* | 11/2018 | Gunasekar | A61B 5/6843 |
| 2018/0368722 A1* | 12/2018 | Lunner | A61B 5/6803 |
| 2019/0121431 A1* | 4/2019 | Lee | G06F 3/011 |
| 2019/0122475 A1* | 4/2019 | Dyne | G07C 9/02 |
| 2019/0159675 A1* | 5/2019 | Sengupta | A61B 5/0476 |
| 2019/0290157 A1* | 9/2019 | Ramer | A61B 5/6814 |
| 2019/0290211 A1 | 9/2019 | Ramer et al. | |
| 2019/0294244 A1* | 9/2019 | Ramer | A61B 5/0478 |
| 2019/0294245 A1* | 9/2019 | Ramer | A61B 5/04001 |

OTHER PUBLICATIONS

Wikipedia, "Consumer Computer Brain-Interfaces", https://en.wikipedia.org/wiki/Consumer_brain%E2%80%93computer_interfaces, searched Dec. 27, 2017 (2 pages).
Entire Prosecution History of U.S. Appl. No. 15/934,083, filed Mar. 23, 2018, entitled "Electroencephalography Control of Controllable Device".
Entire prosecution history of U.S. Appl. No. 15/981,446, entitled "User Preference and User Hierarchy in an Electroencephalography Based Control System," filed May 16, 2018.
Entire prosecution history of U.S. Appl. No. 16/217,543, entitled "Neural Control of Controllable Device," filed Dec. 12, 2018.
Sophia Chen, "Hardwiring the BRAIN fNIRS technology creates an increasingly sophisticated connection between brain and computer," SPIE Professional, Jan. 2019, pp. 22-24.
OSA®, "Fiber Optic Sensor Measures Tiny Magnetic Fields," Sep. 19, 2019, Copyright © 2018 The Optical Society (4 pages).
Non Final Office Action for U.S. Appl. No. 15/934,083, dated Aug. 9, 2019, 9 pages.
Notice of Allowance for U.S. Appl. No. 15/934,083, dated Oct. 9, 2019, 8 pages.
Non Final Office Action for U.S. Appl. No. 15/981,446, dated Oct. 22, 2019, 15, pages.
Notice of Allowance for U.S. Appl. No. 15/981,446, dated Feb. 12, 2020, 11 pages.

* cited by examiner

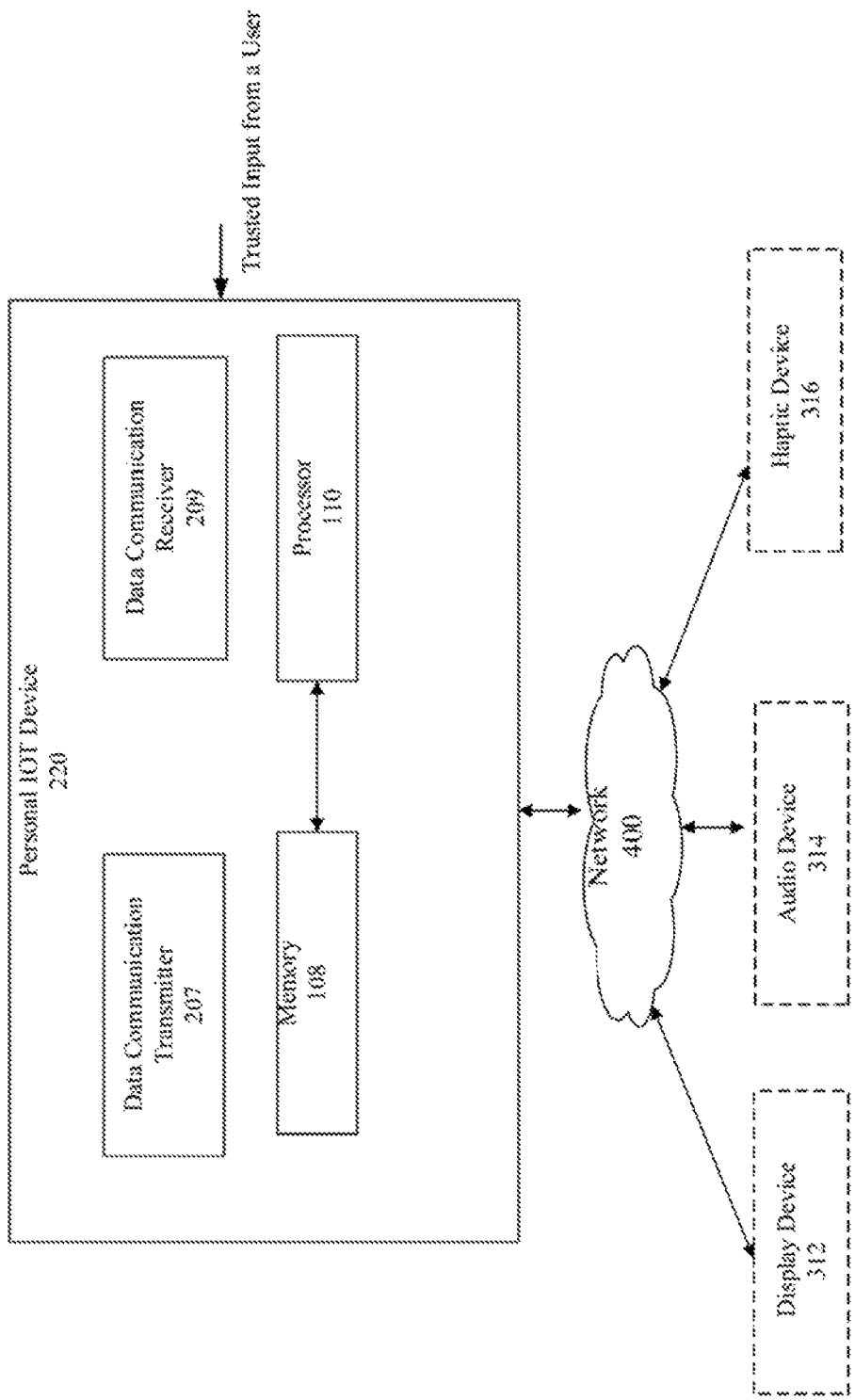

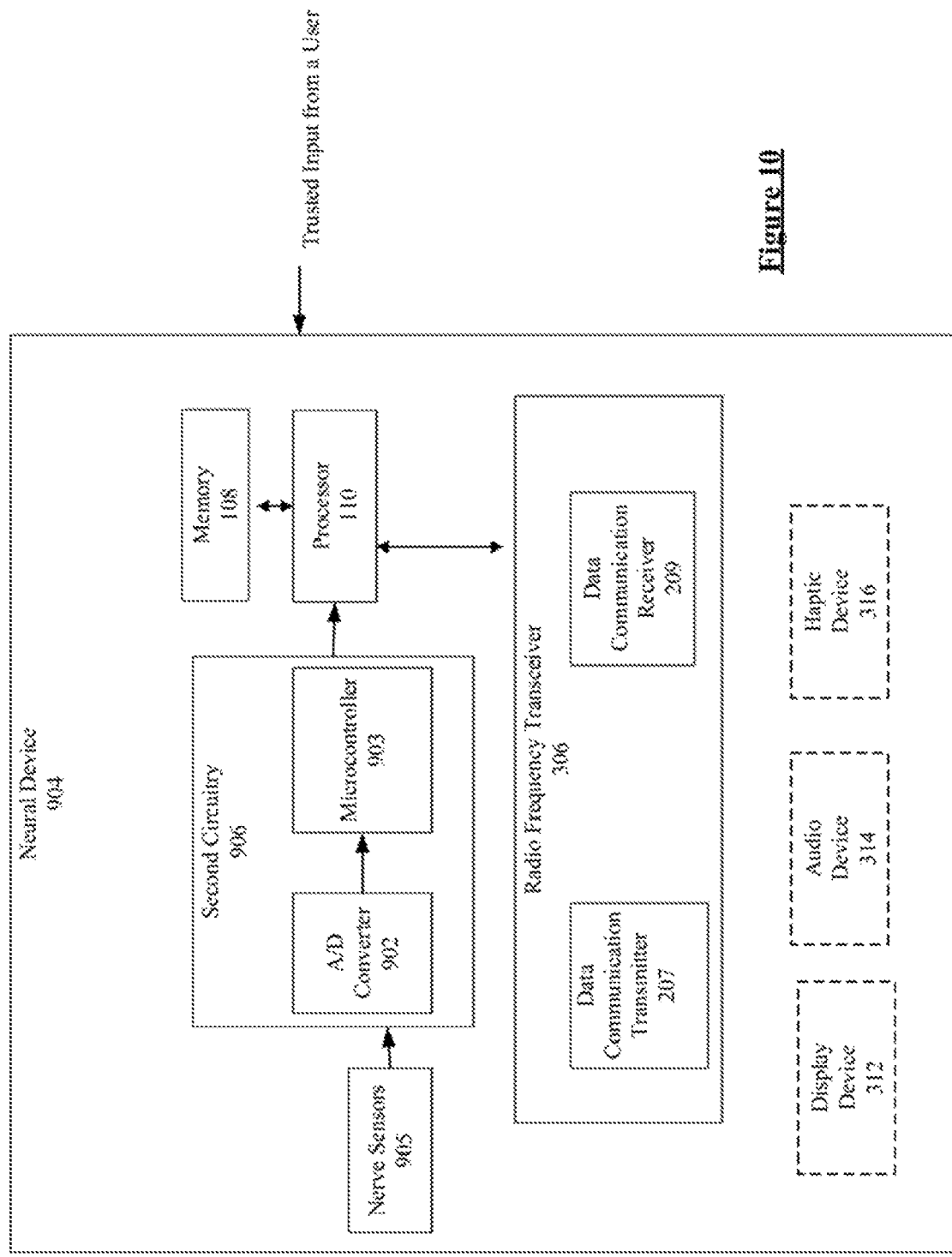

TRAINING OF AN ELECTROENCEPHALOGRAPHY BASED CONTROL SYSTEM

CROSS-REFERENCE TO RELATED APPLICATIONS

This is the Continuation-in-Part of U.S. patent application Ser. No. 15/934,083 filed Mar. 23, 2018, now U.S. Pat. No. 10,551,921, issued Feb. 4, 2020, entitled "ELECTROENCEPHALOGRAPHY CONTROL OF CONTROLLABLE DEVICE, which is incorporated herein by reference in its entirety.

TECHNICAL FIELD

The subject matter of this application is directed toward control systems, more specifically to training of Electroencephalography (EEG) system for control of lighting and/or building management systems (BMS).

BACKGROUND

Electroencephalography (EEG) is an electrophysiological monitoring method to record electrical activity of the brain. It is typically noninvasive, with the electrodes placed along the scalp, although invasive electrodes are sometimes used such as in electroencephalography (EEG) measures voltage fluctuations resulting from ionic current within the neurons of the brain. In clinical contexts, EEG refers to the recording of the brain's spontaneous electrical activity over a period of time, as recorded from multiple electrodes placed on the scalp. Diagnostic applications generally focus either on event-related potentials or on the spectral content of EEG. The former investigates potential fluctuations time locked to an event like stimulus onset or button press. The latter analyzes the type of neural oscillations that can be observed in EEG signals in the frequency domain.

It has been suggested to measure and record the brain's spontaneous electrical activity to train the EEG for control of devices. For example, the U.S. Air Force demonstrated in the 1980s that pilots wearing simple EEG head gear could control computer displays. Such EEG is trained to control the computer displays. Presently, EEG systems are being trained to control things like "quad copters". In fact, EEG sensors may be implemented inside a head of a user. As this technology becomes more prevalent one could imagine that training of the EEG systems to control a wide range of equipment could become pervasive.

In recent years, the sophistication of lighting control systems have increased significantly, for example, offering lighting scene, profile or schedule manipulation for individual lighting devices, for groups of lighting devices or all for lighting devices at a controlled premises. Depending on the technology of the luminaires, control functions may include simple ON/OFF control, intensity control (e.g. dimming) and even control of color characteristics (e.g. for tunable white luminaires or the like). Building automation control (BAC) systems or building management systems (BMS) also have improved in the sophistication of the ability to reach every unit item or controllable appliance at the premises, offer informative, intuitive access to information and readily customizable control operations for every controllable device on the premises that is adapted for BAC or BMS type networked monitoring and control functions.

Currently no such systems exist that train EEG system for control of the lighting operations of the lighting systems and building management operations of the building management system.

SUMMARY

The Examples disclosed herein improve over lighting control systems and BAC systems by providing EEG training methodology for control of the lighting and the building management systems.

An example system includes an electroencephalography (EEG) device configured to be positioned on a head of a user. The EEG device includes one or more electrodes configured to detect EEG signals from the brain of the user. The system also includes a circuitry coupled to the one or more electrodes configured to process the EEG signals detected via the one or more electrodes of the EEG device. The system also includes a processor coupled to or in communication with the circuitry and a memory accessible by the processor. The memory stores data including a control instruction. The memory also stores program instructions, which when executed by the processor configures the processor to generate, based on the control instruction, a control data signal, for control of an operation of a controllable device configured to provide a premises related service in an area of a premises. During a training phase, execution of the program instructions further configures the processor to determine whether or not that the control operation of the control data signal is consistent with the detected EEG signals based on a trusted input from the user, and upon determination that the control operation is consistent with the detected EEG signals, store, in the memory, recognition data characterizing the detected EEG signals as a predetermined set of signals in association with the control instruction.

Another example system includes an electroencephalography (EEG) device configured to be positioned on a head of a user. The EEG device includes one or more electrodes configured to detect EEG signals from the brain of the user. The system also includes a circuitry coupled to the one or more electrodes configured to process the EEG signals detected via the one or more electrodes of the EEG device. The system also includes a processor coupled to or in communication with the circuitry and a memory accessible by the processor. The memory stores data including a control instruction. The memory also stores program instructions, which when executed by the processor configures the processor to generate, based on the control instruction, a control data signal, for control of an operation of a controllable device configured to provide a premises related service in an area of a premises. During a training phase, execution of the program instructions further configures the processor to determine whether or not that the control operation of the control data signal is consistent with the detected EEG signals based on a trusted input from the user, and upon determination that the control operation is not consistent with the detected signals, associate the detected EEG signals with another control instruction in the data. Another control instruction is different from the control instruction. Also, in the training phase, execution of the program instruction further configures the processor to determine that the association is consistent with another control instruction based on another trusted input from the user, and store, in a memory, recognition data characterizing the detected EEG signals as a predetermined set of signals in association with another control instruction.

An example method includes detecting signals from an EEG device and determining whether or not a control operation of a control data signal is consistent with the detected EEG signals based on a trusted input from the user. The control data signal is generated based on a control instruction stored in data for the control operation of a controllable device configured to provide a premises related service. The method also includes that upon determination that the control operation is consistent with the detected EEG signals, storing, in a memory, recognition data characterizing the detected EEG signals as a predetermined set of signals in association with the control instruction.

Another example method includes receiving detected signals from an EEG device and determining whether or not a control operation of a control data signal is consistent with the detected EEG signals based on a trusted input from the user. The control data signal is generated based on a control instruction stored in data for the control operation of a controllable device configured to provide a premises related service. The method also includes that upon determination that the control operation is not consistent with the detected EEG signals, associating the detected EEG signals with another control instruction in the data such that another control instruction is different from the control instruction, determining that the association is consistent based on another trusted input from the user, and storing, in memory, recognition data characterizing the detected EEG signals as a predetermined set of signals in association with another control instruction.

Additional objects, advantages and novel features of the examples will be set forth in part in the description which follows, and in part will become apparent to those skilled in the art upon examination of the following and the accompanying drawings or may be learned by production or operation of the examples. The objects and advantages of the present subject matter may be realized and attained by means of the methodologies, instrumentalities and combinations particularly pointed out in the appended claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 4 is a functional block diagram of an example of a personal Internet of Things (PIOT) device configured for training an EEG based control system for controlling a premises related service provided by a controllable device in an area of premises.

FIG. 10 is a functional block diagram of a neural device of FIG. 9 configured for training of a neuro based control of a premises related service provided by a controllable device in an area of premises.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The term "luminaire" as used herein is intended to encompass essentially any type of device that processes generates or supplies light, for example, for general illumination of a space intended for use of or occupancy or observation, by a person or animal. However, a luminaire may provide light for use by automated equipment, such as sensors/monitors, robots, etc. that may occupy or observe the illuminated space, instead of or in addition to light provided for an organism. However, it is also possible that one or more luminaires in or on a particular premises have other lighting purposes, such as signage for an entrance or to indicate an exit. In most examples, the luminaire(s) illuminate a space or area of a premises to a level useful for a human in or passing through the space, e.g. general illumination of a room or corridor in a building or of an outdoor space such as a street, sidewalk, parking lot or performance venue.

The term "coupled" as used herein refers to any logical, physical or electrical connection, link or the like by which signals, data, instructions or the like produced by one system element are imparted to another "coupled" element. Unless described otherwise, coupled elements or devices are not necessarily directly connected to one another and may be separated by intermediate components, elements or communication media that may modify, manipulate or carry the signals. For example, system elements may be coupled for wired or wireless communication, including without limitation radio frequency (RF), light fidelity (LiFI), fiberoptic, ultrasonic or the like in the discussions below.

Various examples disclosed herein relate to an EEG training methodology for a system configured to control lighting and building management. Examples described below encompass systems utilizing EEG training functionality to control various BAC appliances, lighting devices, etc. that control a service in an area of a premise. Such service may include but is not limited to light, heating, ventilation and air conditioning (HVAC), door access, fire and safety equipment, on-premises surveillance, etc.

Reference is now made in detail to the examples illustrated in the accompanying drawings and discussed below.

Figure 1:
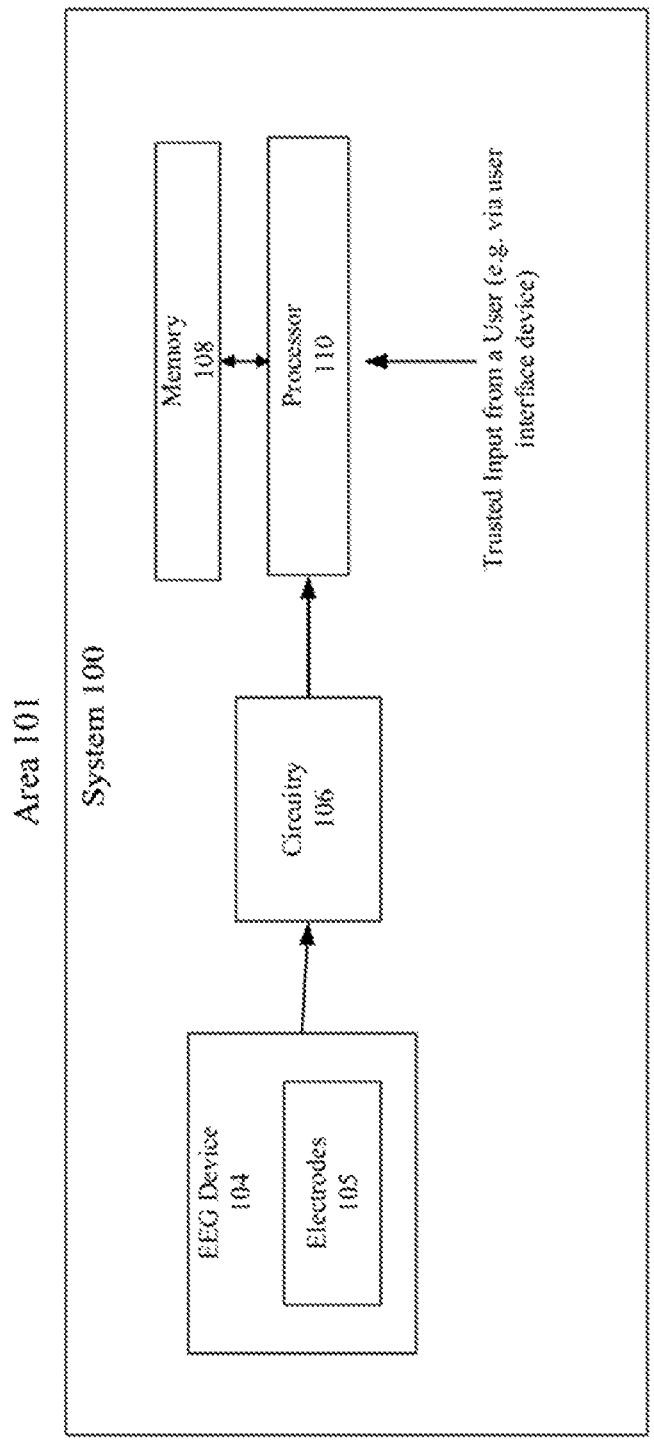
FIG. 1 illustrates one example of an EEG system for training equipment for EEG based control of a premises related service provided by a controllable device in an area of a premises.

The example of FIG. 1 illustrates an EEG system (system) 100 for training equipment for EEG based control of a premises related service in an area 101 of a premises. Some of the premises related services include but are not limited to light, heating, ventilation and air conditioning (HVAC), door access, fire and safety equipment, on-premises surveillance, etc.

The system 100 includes an electroencephalography (EEG) device 104, which is configured to be positioned with respect to a head of a user in the area 101. In one example, the EEG device 104 is an EEG headset placed on top of the user's head. In another example, the EEG device 104 is an EEG sensor implanted inside the user's head. The EEG device 104 includes one or more electrodes 105 configured to detect signals from a brain of the user. The system 100 also includes a circuitry 106 coupled to the electrodes 105 to process the signals detected by the electrodes 105. In one example, the signals are sets of signals detected by the electrodes 105 in real time. In one example, the signals are EEG signals detected by the electrodes 105 prior to real time. In another example, the signals are sets of neural signals (e.g. nerve signals (see FIGS. 9 and 10) alone or in combination with EEG signals.

In one implementation, the system 100 includes a memory 108 that stores data, which includes a plurality of control instructions. A control instruction corresponds to controlling the premises related service provided in the area 101. The system 100 also includes a processor 110, which is coupled to the circuitry 106 to receive the processed sets of detected EEG signals. The memory 108 also stores instructions, which is accessible by the processor 110 such that execution of the instructions by the processor 110 to perform various functions described herein.

In one implementation, the processor 110 generates a control data signal based on a control instruction among the plurality of control instructions stored in the memory 108. The control data signal corresponds to a control operation among a plurality of control operations of a controllable device (See FIG. 1A) configured to perform the control operation. The control operation controls the premises related service in the area 101. In one example, the processor 110 converts the control instruction into a control data signal, which includes an operation related to controlling premises related service in the area 101. The memory 108 also stores instructions, which is accessible by the processor 110 such that in a training phase, execution of the instructions by the processor 110 to perform various functions described herein.

In one implementation, in the training phase, the processor 110 determines whether or not the control operation of the control data signal is consistent with the detected EEG signal based on a trusted input received from a user. In one example, the user is the user of the EEG device 104. In one example, the trusted input is a positive trusted input, which includes a user's approval of the control operation. In another example, the positive trusted input may include user selection of the control operation. In one example, the trusted input includes a negative trusted input, which includes a user's disapproval of the control operation. In another example, the negative trusted input includes a user's selection of another control operation among the plurality of control operations. This another control operation is different from the control operation corresponding to the control data signal generated by the processor 110.

In one implementation, the user input is received via a user responsive element. In one example, the user responsive element is a user device with input capability and output capability (e.g. a display device, an audio device or a haptic device (See FIG. 2)). Examples of such user devices may include mobile devices, desktop or portable personal computers or similar computer devices, or user devices specifically configured for use in the EEG training. In another example, the user responsive element is a manual control of a controllable device (See FIG. 1A) by the user. For example, the control operation functionality may result in the control data signal, which is transmitted to a controller (See FIG. 1A), which functions to automatically turn off the lights in the area 101, and the user of the EEG device 104 manually operates a wall switch or button or the like to turn on the lights. The processor 110 might interpret the manual operation to turn on the lights right after system turn off of the lights, i.e. another control operation, as a disapproval or other negative trusted input. The system might then undo the previous operation and/or update stored data as part of the training. In one example, the control data signal associated with another control operation of turning on the lights is sent and received via a RF transceiver of a network (not shown).

In one example, the user responsive element is a function of the EEG device 104 such that the trusted input (positive or negative) is based on detection of EEG signals indicating one or more of the approval of the control operation, disapproval of the control operation, selection of the control operation and selection of another control operation, which is different from the control operation. In another example, the user responsive element is a reaction or behavior of the user of the EEG device 104 such that the trusted input (positive or negative) is received as a function of the reaction or behavior of the user of the EEG device 104. For example, the user of the EEG device 104 may indicate satisfaction (e.g. smile by the user or nod by the user), which is interpreted as positive trusted input, i.e. the approval of the control operations. In another example, the user of the EEG device 104 may indicate annoyance (e.g. roll his eyes or shake his head), which is interpreted as the negative trusted input, i.e. disapproval of the control operation. In a further example, the user responsive element is a gesture (e.g. some type of movement) by the user of the EEG device 10 such that the trusted input (positive or negative) is received as a function of the gesture by the user of the EEG device 104. For example, the control operation functionality results in control data signals which is transmitted to a controller (see FIG. 1A), which functions to automatically turns off the lights and the user raises her hand, which is interpreted as turn on the lights, i.e. another control operation.

In one implementation, a passive acceptance by a user is interpreted as the positive trusted input, i.e. the approval of the control operation. For example, the user of the EEG device 104 is inactive (i.e. does not take any action related to the control operation or use the responsive element to indicate any type of the trusted input) in response to the control operation, which is interpreted as the positive trusted input.

In one example, the processor 110 receives the positive trusted input as the trusted input. As a result, the processor 110 determines that the control operation is consistent with the detected EEG signals. In one implementation, when the processor 110 determines that the control operation is consistent with the detected EEG signals, the processor 110 stores in the memory 108 recognition data characterizing the detected EEG signals as a predetermined set of signals, which are associated with the control instruction among the plurality of instructions. In one example, the processor associates the detected EEG signals with the control instruction in the data. In one implementation, the processor 110 generates the control data signal corresponding to the control instruction in the training phase. In another implementation, processor generates the control data signal corresponding to the control instruction in real-time operational phase.

In one implementation, the EEG device 104 detects additional EEG signals at a later time after the detection of the EEG signals. In one example, the later time is during training phase. In another example, the additional the later time is during real-time operational phase. In one implementation, the processor 110 uses the stored data to interpret the additional EEG signals. Specifically, the processor 110 analyzes the additional EEG signals to determine that the additional EEG signals correspond to the control instruction. In one implementation, the processor 110 generates the control data signal based on the control instruction and determines whether or not the control operation of the control data signal is consistent with the additional EEG signals based on another trusted input received from the user. Another trusted input is similar to the trusted input such that another trusted input is one of the positive trusted input or the negative trusted input as discussed above. In one example, the processor 110 receives the positive trusted input as another trusted input As a result, the processor 110 determines that the control operation is consistent with the additional EEG signals. The processor 110 stores in the memory 108 recognition data characterizing the additional EEG signals as predetermined set of signals, which are associated with the control instruction among the plurality of instructions. In another example, the processor 110 receives the negative trusted input as another trusted input. As a result, the processor 110 determines that the control operation is not consistent with the additional EEG signals and modifies the recognition data stored in the memory 108. As discussed above, the recognition data characterizes the EEG signals as the pre-determined set of signals in association with the control instruction. Specifically, the processor 110 identifies another control instruction among the plurality of control instructions stored in the memory 108. The processor 110 stores in the memory 108 the recognition data characterizing the additional EEG signals as another predetermined set of signals in association with another control instruction.

In another implementation, during the training phase, the processor 110 receives the negative trusted input as the trusted input. As a result, the processor 110 determines that the control operation is not consistent with the detected EEG signals. In one implementation, when the processor 110 determines that the control operation is inconsistent with the detected EEG signals, the processor 110 associates the detected EEG signals with another control instruction among the plurality of control instructions in the data. Another control instruction is different from the control instruction. In one implementation, the processor 110 determines whether the association of the detected EEG signals is consistent with another control instruction based on another trusted input from the user of the EEG device 104. Another trusted input is similar to the trusted input such that another trusted input is one of the positive trusted input or the negative trusted input as discussed above. In one example, the processor 110 receives the positive trusted input as another trusted input. As a result, the processor 110 determines that the association of the detected EEG signals is consistent with another control instruction and stores in the memory 108, memory recognition data characterizing the detected EEG signals as predetermined set of signals associated with another control instruction. In one implementation, the processor 110 generates another control data signal corresponding to another control instruction in the training phase. Another control data signal is different from the control data signal. In another implementation, the processor 110 generates another control data signal corresponding to another control instruction in the real-time operational phase.

Figure 1A:
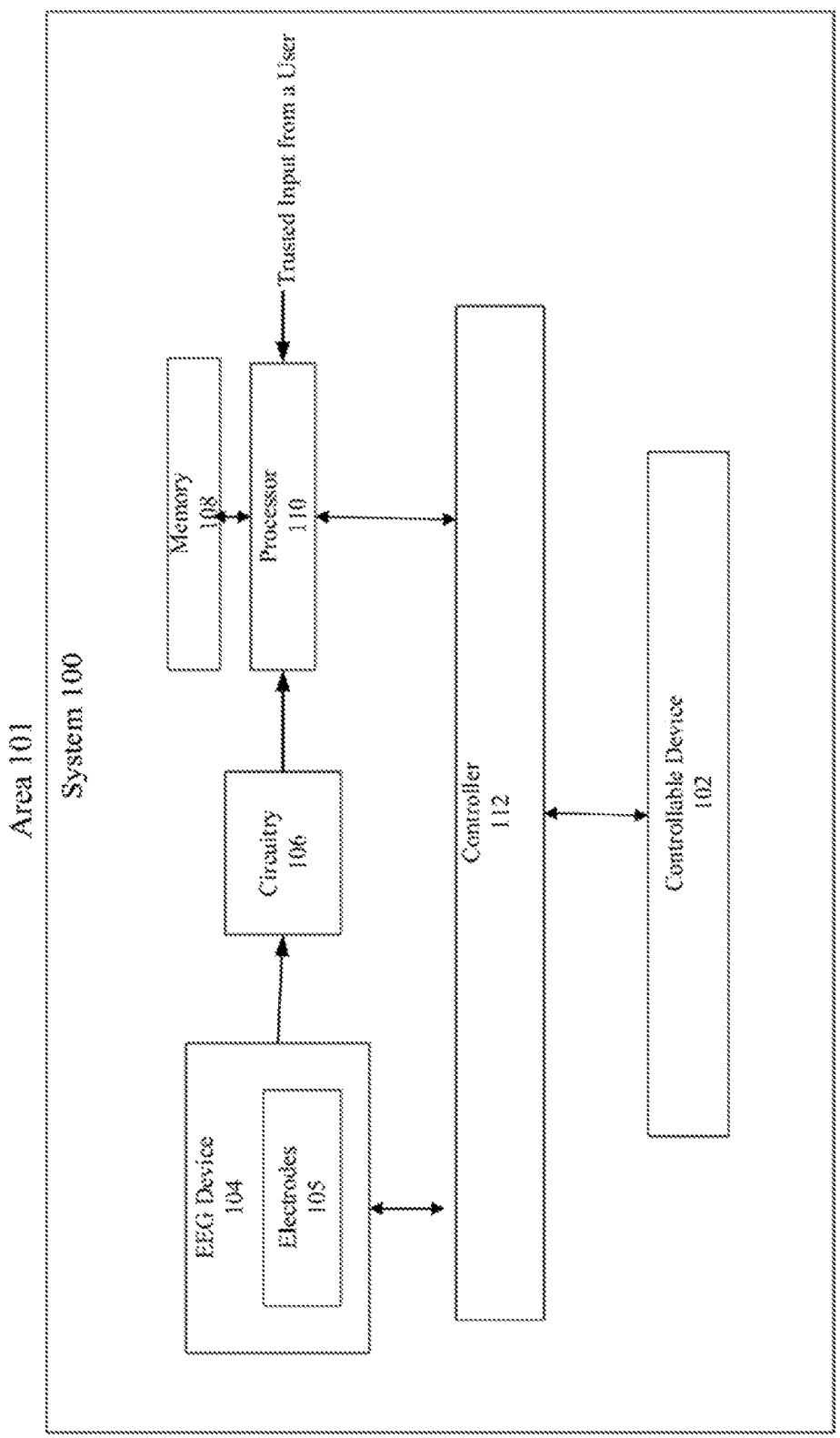
FIG. 1A illustrates another example of an EEG system including training for controlling a premises related service provided by a controllable device in an area of a premises.

FIG. 1A includes an example of the system 103, which includes the same components of system 100 and further includes a controllable device 102 and a controller 112. As illustrated, the controller 112 is coupled to or in communication with the controllable device 102 and the processor 110. Such controllable device 102 may include luminaire, various BAC appliances etc. In one example, the controllable device 102 is a luminaire such that the control instruction provides instruction on controlling the luminaire. In another example, the controllable device 102 is a BAC appliance such that the control instruction provides instruction on controlling the BAC appliance. The processor 110 selects one of the luminaire or the BAC appliance based on the control instruction. The processor 110 generates a control data signal for the selected luminaire or the BAC appliance based on the at least one control instruction. In one example, the controller 112 is an intelligent element integrated in the controllable device 102. In another example, that the controller is a centralized controller controlling a plurality of similar controllable devices, (e.g. wall switch or like controlling a number of the luminaires or a building management control system (control the controllable device and other types of devices within the premises).

In one implementation, the processor 110 transmits the control data signal to a controller 112, which controls the premises related service provided by the controllable device 102 (selected luminaire or the BAC appliance) in the area 101. In one implementation, the controller 112 controls the premises related service in a real time operational phase. Some examples of controlling the premises related services include but are not limited to turning lights on or off, dimming lights, color temperature, color red green blue, circadian rhythm, chaotic program, individual luminaire control, occupancy sensing, decrease or increase level of one of heating, cooling or air, open or close doors, open or close the doors, turn on or off the television, decrease or increase the sound of alarm system etc.

In one implementation, the EEG device 104 is configured or provisioned to generate and send the control instruction in an appropriate format for controlling the lighting system or the BAC appliance system in the area 101. In one implementation, the EEG training would not be repeated when the EEG device 104 is located in an area or location that is different from the area 101 utilizing another system that is different from the system 100. In one implementation, at a different area, the EEG device 104 is configured or provisioned to operate with the different system at the different area or location. Provisioning of a device to operate on a network usually entails some input of data to the device and/or the network to set up device communications via the network. If the device supports multiple communication bands and protocols, the provisioning may also inform the device which band(s) and/or what protocol to use for control communications at the premises. If also needed, configuration may involve storing profile data or the like in the device and/or the network defining user privileges when using the system and/or providing access to some or all of the control services the system offers that will available to the user of the particular device. For example, a user of the EEG device 104 would be provided with configuration or provisioning data for the different system with options to select to configure the EEG device 104 with the different system in the different area. As such, the EEG device 104 may be used at multiple different locations with multiple different lighting systems and/or BAC appliance systems, based upon provisioning or commissioning for operation on each system, but without a need to retrain the EEG functionality.

In some implementations, in a real-time operational mode (occurring during training phase or after training phase), the processor 110 determines that EEG detected signals do not correspond to one of the plurality of pre-determined sets of signals stored in the memory 108. As such, the processor 110 does not recognize such EEG detected signals as a known instruction for operation of lighting or other building management systems. In one example, the processor 110 ignores such detected signals during an operational phase that does not involve ongoing training. In another example where the system supports training during otherwise normal operations, the processor 110 may search for other types of pre-determined sets of signals that support other types of inputs, e.g. PIOT device supports control instructions to other types of equipment (e.g. a Television set). As discussed above, in one example, in the training mode, the system updates relevant data such as the pre-determined set of signals and corresponding control instruction when the EEG signals are not recognized as a known instruction. For example, the system updates the pre-determined set of signals based on another trusted user input received from the user indicating the actual type of control operation, which corresponds to the control instruction that the user intended to input by the detected EEG signals.

In one implementation, training of the EEG is specific to each type of the EEG device. Each EEG device may differ in number of electrodes, number of EEG signals etc. In one example, a first EEG device is trained to adapt to a first set of EEG signals such that the first set of signals are mapped to one or more control instructions in the memory 108. A second EEG device, which is different from the first EEG device would transmit a second set of BEG signals. In one example, all of the second set of EEG signals are different from the first set of EEG signals. Accordingly, the second EEG device would need to be completely retrained to map the second set of EEG signals with one or more control instructions in the memory 108. In another example, a first number of the second set of EEG signals of the second EEG device are same as the first set of EEG signals in the first EEG device and a second number of the second set of EEG signals of the second EEG device are different from the first set of EEG signals from the first EEG device. Accordingly, the second EEG device would need to be partially trained such that processor 110 would adapt to optimize to train only to the second number of the second set of EEG signals of the EEG device to map the second number of the second set of EEG signals to one or more control instructions in the memory 108. In one implementation, when the first number of the second set of EEG signals of the second EEG device are same as the first set of EEG signals of the first EEG device, the training of the first set of EEG signals are downloaded into the system such that the one or more control instructions are mapped to the first number of the second set of EEG signals of the second EEG device. In one example, the second EEG device is passively trained with continuous training such only the second number of the second set of EEG signals would be trained to map to one or more control instructions in the memory 108. In another example, the second EEG device is actively trained such that all the second set of EEG signals are trained similarly to the training of the first set of signals in the first EEG device to map all the second set of EEG signals to one or more control instructions in the memory 108. In one implementation, training can take place ahead of the time (before product release/commissioning), in the field at about the same time as provisioning/commissioning on a first control system, or as an on-going optimization during an operational control phase.

Figure 2:
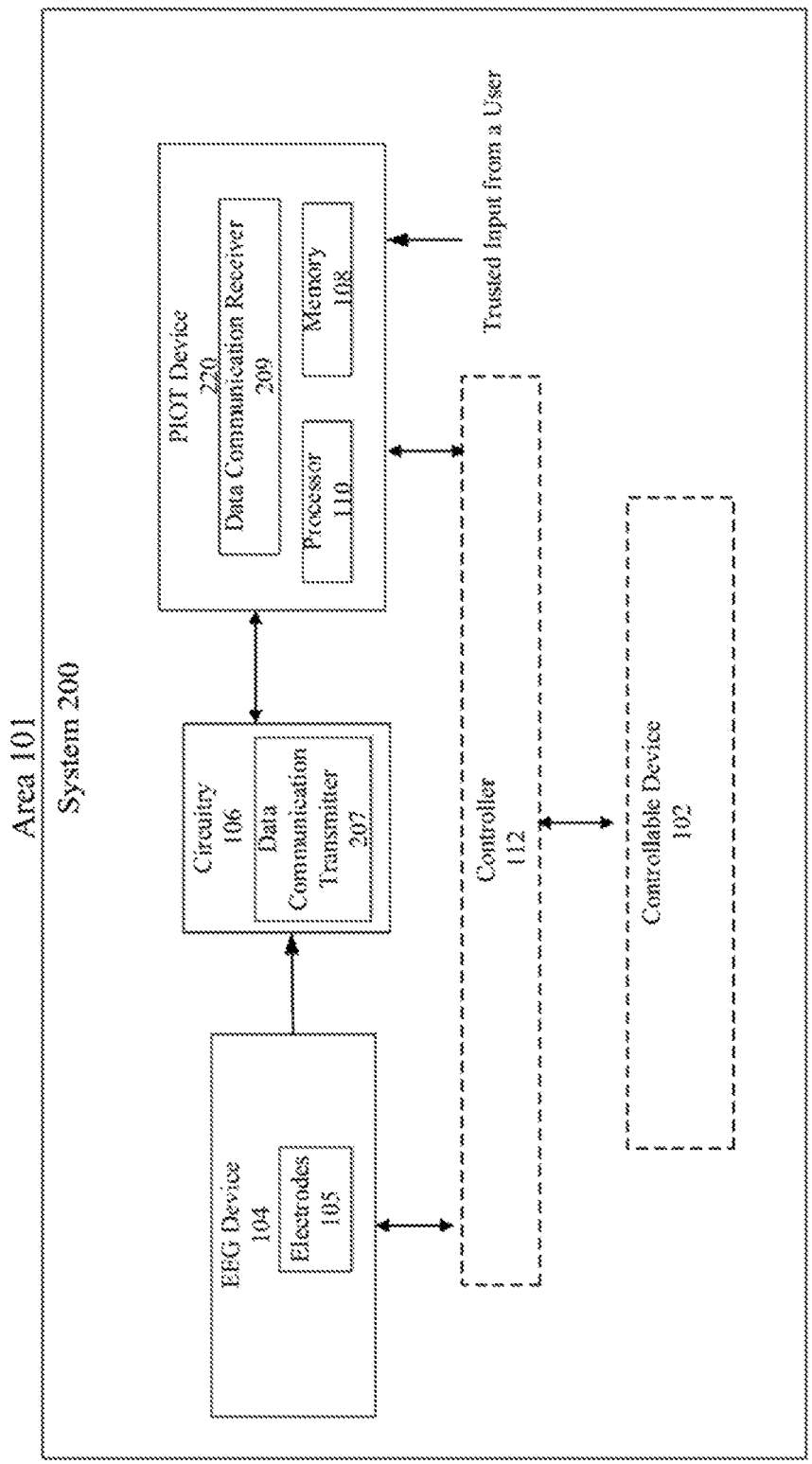
FIG. 2 illustrates another example of an EEG system for including training for controlling a premises related service provided by a controllable device in an area of a premises.

FIG. 2 includes an example of the system 200, which includes the same components of system 100 and the circuitry 106 further includes a data communication transmitter 207. The system 200 also includes a personal Internet of Things (PIOT device) 220 including the memory 108 and the processor 110 and further including a data communication receiver 209. The data communication receiver 209 is compatible with the data communication transmitter 207 of the circuitry 106. In one example, the data communication transmitter 207 is a radio frequency (RF) transmitter configured to transmit data over RF spectrum. In another example, the data communication receiver 209 is a RF receiver configured to transmit data over the RF spectrum.

The RF spectrum or "radio spectrum" is a non-visible part of the electromagnetic spectrum, for example, from around 3 MHz up to approximately 3 THz, which may be used for a variety of communication applications, radar applications, or the like. In the discussions above, the RF transmitted and received for network communication, e.g. Wifi, BLE, Zigbee etc., was also used for controlling lighting or a building management control system, in the frequencies bands/bandwidths specified for those standard wireless RF spectrum data communication technologies. In another implementation, the network communications media may be wired, fiberoptic, LiFI, ultrasonic or the like.

In another implementation, the transceiver is an ultra-wide band (also known as UWB, ultra-wide band and ultraband) transceiver. UWB is a radio technology that can use a very low energy level for short-range, high-bandwidth communications over a large portion of the radio spectrum. UWB does not interfere with conventional narrowband and carrier wave transmission in the same frequency band. Ultra-wideband is a technology for transmitting information spread over a large bandwidth (>500 MHz) and under certain circumstances be able to share spectrum with other users. Ultra-wideband characteristics are well-suited to short-distance applications, such as short-range indoor applications. High-data-rate UWB may enable wireless monitors, the efficient transfer of data from digital camcorders, wireless printing of digital pictures from a camera without the need for a personal computer and file transfers between cell-phone handsets and handheld devices such as portable media players. UWB may be used in a radar configuration (emitter and deflection detection at one node) for real-time location systems and occupancy sensing/counting systems; its precision capabilities and low power make it well-suited for radio-frequency-sensitive environments. Another feature of UWB is its short broadcast time. Ultra-wideband is also used in "see-through-the-wall" precision radar-imaging technology, precision detecting and counting occupants (between two radios), precision locating and tracking (using distance measurements between radios), and precision time-of-arrival-based localization approaches. It is efficient, with a spatial capacity of approximately 1013 bit/s/m$^2$. In one example, the UWB is used as the active sensor component in an automatic target recognition application, designed to detect humans or objects in any environment.

In one implementation, the memory 108 stores user identification data for each of a plurality of user identifiers. In one example, the user identification data is uniquely associated with the EEG device 104 identifying a user among a plurality of users of the EEG device 104 in the area 101 of the premises. In another example, the user identification data is uniquely associated with the PIOT device 220 identifying a user of the PIOT device 220 identifying a user among the plurality of users of the PIOT device 220 in the area 101 of the premises. The user's location is tracked based on the user identification data associated with one or both of the EEG device 104 or the PIOT device 220.

In one implementation, the memory 108 also stores a plurality of hierarchical classes of user(s) as member(s) with each class having permissions to use one or more control instructions among the plurality of control instructions. Some examples of classes of users include, building administrator, employee, guest etc. For example, the building administrator has permissions to all the control instructions while the guest may only have permissions to one or two control instructions. In one implementation, the data communication receiver 209 receives a user identification data from the EEG device 104. In one implementation, the data communication receiver 209 receives a user identification data directly from the PIOT device 220. The processor 110 utilizes the received user identification data to search the memory 108 to identify the user among the plurality of users and the corresponding hierarchy class of the identified user of which the user is the member. In one implementation, the processor 110 transmits the control data signal to the controller 112 that relates to the one or more control instructions permitted for the corresponding hierarchy class. The controller 112 controls the premises related service provided by the controllable device 102 (selected luminaire or the BAC appliance) in the area 101 based on the permitted one or more control instructions.

In one implementation, the data communication receiver 209 receives identifying data from the controller 112. The identifying data includes but is not limited to location of the controller in the area, communication capabilities of the controller, control operations supported by the controller, types of controllable devices controlled by the controller, controller variables for each type of controllable device, or combinations thereof.

In one example, the communication capabilities are supported by the EEG device 104. In another example, the communication capabilities are supported by the PIOT device 220. The control operations supported by the controller may include light related control operations, building related control operations etc. Some of the light related control operations include turning lights on/off, dimming lights, color temperature, color red green blue, circadian rhythm, chaotic program etc. Building related control operations include heating/cooling & air control, door access controls, fire and safety control, on-premises surveillance control etc. As discussed above, type of controllable device includes luminaire, various BAC appliances etc. The controllable variables for each type of the controllable device are variables specific to the controllable device. In one example, the controllable variables may include but are not limited to various types of color characteristics, intensity of light, tuning light, rate of air flow, humidity level, temperature range, open/close of the doors/windows etc. The memory 108 also stores instructions, which is accessible by the processor 110 such that execution of the instructions by the processor 110 to perform various functions described herein.

In one implementation, the processor 110 determines a communication capability among the plurality of communication capabilities of the controller based on the identifying data. The processor 110 functions to adapt at least one aspect of the control data signal based on the determined communication capability of the controller 112. In one example, the processor 110 adapts to a format of the command signal of the control data signal to match with the command signal protocol of the determined communication capability. In another implementation, the processor 110 determines a type of the controllable device 102 among the plurality of types of controllable devices based on the identifying data. In one implementation, the processor 110 adapts the control data signal to the determined type of the controllable device 102. In one example, the controllable device 102 is white LED luminaire that supports ON/OFF and dimming functions, thus the processor 110 adapts the control data signal associated with the control instruction to turn the white LED luminaire ON/Off or dim the white LED luminaire. In another example, the controllable device 102 is a specific LED luminaire that supports a specific intensity variation (such as 10%, 20% etc.) among the several intensity variations of the dimming functions, thus the processor 110 adapts the control data signal associated with the control instructions to the specific intensity variation of the dimming function of the specific Led luminaire. In a further example, the controllable device 102 is a HVAC component that supports functions such as increase/decrease in temperature in the area, thus the processor 110 adapts the control data signal associated with the control instruction to increase or decrease the temperature in the area.

In one implementation, the processor 110 retrieves data identifying control operations supported by the controller based on the identifying data from the controller 112. As discussed above, the control operations supported by the controller may include light related control operations, building related control operations etc. Some of the light related control operations include turning lights on/off, dimming lights, color temperature, color red green blue, circadian rhythm, chaotic program etc. Building related control operations include heating/cooling & air control, door access controls, fire and safety control, on-premises surveillance control etc.

In one implementation, the processor 110 sends the data identifying control operations to an output device (not shown) of the user via the data communication transmitter 207. In one example the control instruction corresponds to a user selection of a control operation among the identified control operations supported by the controller 112.

In one implementation, the memory 108 stores user preference data associated with the user identification data. In one example, the user preference data includes preferred user selection of one or more control operations among the identified control operations in the identifying data that are supported by controller 112 in the area 101. In one implementation, upon receipt of the identifying data, the processor 110 accesses the memory 108 to retrieve the user preference data for the user associated with the controller 112. The processor 110 sends the user preference data to an output of the user device (not shown). In one example the control instruction corresponds to the user preference data including the preferred user selection of the one or more control operations among the identified control operations supported by the controller 112.

Figure 3:
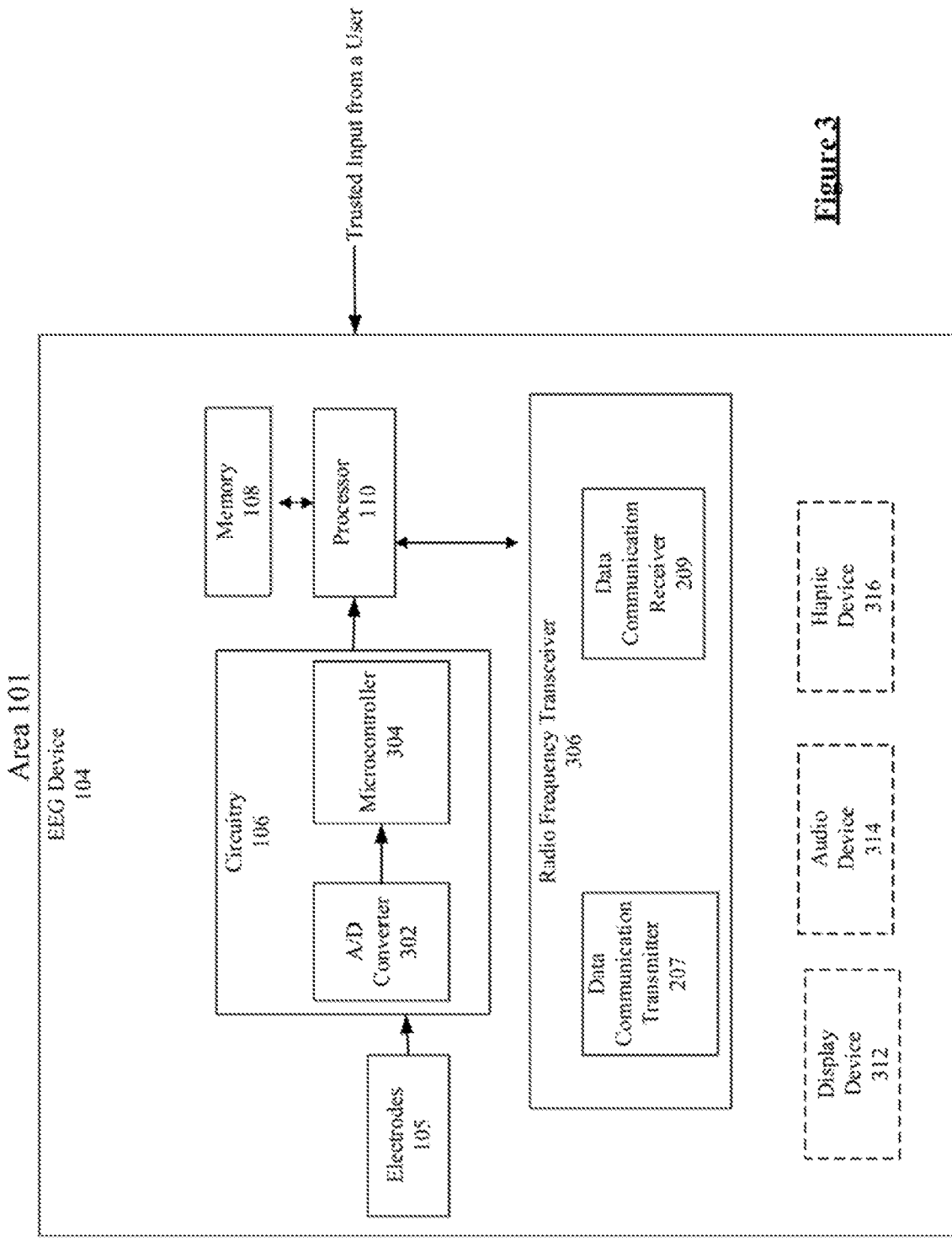
FIG. 3 is a functional block diagram example of an EEG device configured for training of an EEG based control of a premises related service provided by a controllable device in an area of a premises.

FIG. 3 includes an example of an EEG device 104 of FIG. 1. In this example, besides the electrodes 105, the EEG device 104 also includes the circuitry 106, the memory 108 and the processor 110. As shown, the circuitry 106 includes an analog to digital (A/D) converter 302 and a microcontroller 304. As discussed above, the circuitry 106 processes the EEG signals detected by the electrodes 105. The EEG signals detected by the electrodes 105 are analog signals. In one example, A/D converter 302 converts the analog signals into digital signals and the microcontroller 304 microcontroller 304 assembles the digital signals outputted from the A/D converter 302 into a format for a transmission to the processor 110.

The EEG device 104 includes a radio frequency (RF) transceiver 306 coupled to the processor 110. The RF transceiver 306 includes the data communication transmitter 207 and the data communication receiver 209. The data communication receiver 209 receives data over the RF spectrum. The data communication transmitter 207 transmits the received data over the RF spectrum to a user device (e.g. display device 312, audio device 314, and haptic device 316) of the user integrated in the EEG device. As discussed above, the memory stores data including the control instruction and based on the control instruction, the processor 110 generates the control data signal, which corresponds to a control of an operation of the controllable device, which provides a premises related service in the area 101. The processor 110 is coupled to the circuitry 106 and thus configures the EEG device 104 to receive the data regarding the detected EEG signals and determines whether or not the control operation of the control data signal is consistent with the detected EEG signals based on a trusted input from the user. As discussed above, upon determination that the control operation is consistent with the detected EEG signals, the processor 110 stores in the memory 108, recognition data characterizing the detected EEG signals as predetermined set of signals in association with the control instruction. Also, as discussed above, upon determination that the control operation is not consistent with the detected EEG signals, the processor 110 associates the detected EEG signals with another control instruction in the data, determines that the association is consistent upon another trusted input from the user and stores in the memory 108 recognition data characterizing the detected signals s pre-determined set of signals in association with another control instruction as discussed in detail above with respect to FIG. 1.

As discussed above, in one implementation, the memory 108 stores the user identification data uniquely associated with the EEG device 104 identifying a user among a plurality of users of the EEG device 104 in the area 101 of the premises. Also discussed above, in one implementation, the memory 108 also stores a plurality of hierarchical classes of user(s) as member(s) with each class having permissions to use one or more control instructions among the plurality of control instructions. In one implementation, the data communication receiver 209 receives a user identification data of the EEG device 104. As discussed above, the processor 110 utilizes the received user identification data to search the memory 108 to identify the user among the plurality of users and the corresponding hierarchy class of the identified user of which the user is the member. The processor 110 transmits the control data signal to the controller 112 that relates to the one or more control instructions permitted for the corresponding hierarchy class.

As discussed above, in one implementation, the data communication receiver 209 receives identifying data from the controller 112. Also, as discussed above, the identifying data includes but is not limited to location of the controller in the area, communication capabilities of the controller, control operations supported by the controller, types of controllable devices controlled by the controller, controller variables for each type of controllable device, or combinations thereof.

As discussed above, in one implementation, the processor 110 determines a communication capability among the plurality of communication capabilities of the controller based on the identifying data. The processor 110 functions to adapt at least one aspect of the control data signal based on the determined communication capability of the controller 112. Also, as discussed above, in another implementation, the processor 110 determines a type of the controllable device 102 among the plurality of types of controllable devices based on the identifying data. In one implementation, the processor 110 adapts the control data signal to the determined type of the controllable device 102.

As discussed above, in one implementation, the processor 110 retrieves data identifying control operations supported by the controller based on the identifying data from the controller 112. The processor 110 sends the data identifying control operations to an output device (e, g, display device 312, audio device 314 and haptic device 316) of the user via the data communication transmitter 207. In one example, the control instruction corresponds to a user selection of a control operation among the identified control operations supported by the controller 112.

As discussed above, in one implementation, the memory 108 stores user preference data associated with the user identification data. In one example, the user preference data includes preferred user selection of one or more control operations among the identified control operations in the identifying data that are supported by controller 112 in the area 101. Also, as discussed above, in one implementation, upon receipt of the identifying data, the processor 110 accesses the memory 108 to retrieve the user preference data for the user associated with the controller 112. The processor 110 sends the user preference data to an output device (e.g. display device 312, audio device 314 and the haptic device 316) of the user device via the data communication transmitter 207. In one example the control instruction corresponds to the user preference data including the preferred user selection of the one or more control operations among the identified control operations supported by the controller 112.

FIG. 4 includes an example of a PIOT device 220 of FIG. 2. As illustrated, the PIOT device 220 includes the memory 108 and the processor 110, the data communication transmitter 207 and the data communication receiver 209. In one implementation, the data communication receiver 209 receives data over the RF spectrum. In one implementation, the data communication transmitter 207 transmits the received data over the RF spectrum to a user device (e.g. display device 312, audio device 314, and haptic device 316). The data communication transmitter 207 transmits the received data to the user device via a network 400 as shown in FIG. 4. In one example, the network 400 is a RF wireless communication network.

As discussed above, the memory stores data including the control instruction and based on the control instruction, the processor 110 generates the control data signal, which corresponds to a control of an operation of the controllable device, which provides a premises related service in the area 101. In one implementation, the processor 110 is coupled to the data communication receiver 209 and thus also configures the PIOT device 220 to receive the data regarding the detected signals (EEG or nerve signals) and determines whether or not the control operation of the control data signal is consistent with the detected EEG signals based on a trusted input from the user. As discussed above, upon determination that the control operation is consistent with the detected EEG signals, the processor 110 stores in the memory 108, recognition data characterizing the detected EEG signals as predetermined set of signals in association with the control instruction. Also, as discussed above, upon determination that the control operation is not consistent with the detected EEG signals, the processor 110 associates the detected EEG signals with another control instruction in the data, determines that the association is consistent upon another trusted input from the user and stores in the memory 108, recognition data characterizing the detected EEG signals as pre-determined set of signals in association with another control instruction as discussed in detail above with respect to FIG. 1.

As discussed above, in one implementation, the memory 108 stores the user identification data uniquely associated with the PIOT device 220 identifying a user among a plurality of users of the PIOT device 220 in the area 101 of the premises. Also discussed above, in one implementation, the memory 108 also stores a plurality of hierarchical classes of user(s) as member(s) with each class having permissions to use one or more control instructions among the plurality of control instructions. In one implementation, the data communication receiver 209 receives a user identification data of the PIOT device 220. As discussed above, the processor 110 utilizes the received user identification data to search the memory 108 to identify the user among the plurality of users and the corresponding hierarchy class of the identified user of which the user is the member. The processor 110 transmits the control data signal to the controller 112 that relates to the one or more control instructions permitted for the corresponding hierarchy class.

As discussed above, in one implementation, the data communication receiver 209 receives identifying data from the controller 112. Also, as discussed above, the identifying data includes but is not limited to location of the controller in the area, communication capabilities of the controller, control operations supported by the controller, types of controllable devices controlled by the controller, controller variables for each type of controllable device, or combinations thereof.

As discussed above, in one implementation, the processor 110 determines a communication capability among the plurality of communication capabilities of the controller based on the identifying data. The processor 110 functions to adapt at least one aspect of the control data signal based on the determined communication capability of the controller 112. Also, as discussed above, in another implementation, the processor 110 determines a type of the controllable device 102 among the plurality of types of controllable devices based on the identifying data. In one implementation, the processor 110 adapts the control data signal to the determined type of the controllable device 102.

As discussed above, in one implementation, the processor 110 retrieves data identifying control operations supported by the controller based on the identifying data from the controller 112. The processor 110 sends the data identifying control operations to an output device (e, g, display device 312, audio device 314 and haptic device 316) of the user via the data communication transmitter 207. In one example, the control instruction corresponds to a user selection of a control operation among the identified control operations supported by the controller 112.

As discussed above, in one implementation, the memory 108 stores user preference data associated with the user identification data. In one example, the user preference data includes preferred user selection of one or more control operations among the identified control operations in the identifying data that are supported by controller 112 in the area 101. Also, as discussed above, in one implementation, upon receipt of the identifying data, the processor 110 accesses the memory 108 to retrieve the user preference data for the user associated with the controller 112. The processor 110 sends the user preference data to an output device (e.g. display device 312, audio device 314 and the haptic device 316) of the user device via the data communication transmitter 207. In one example the control instruction corresponds to the user preference data including the preferred user selection of the one or more control operations among the identified control operations supported by the controller 112.

Figure 5A:
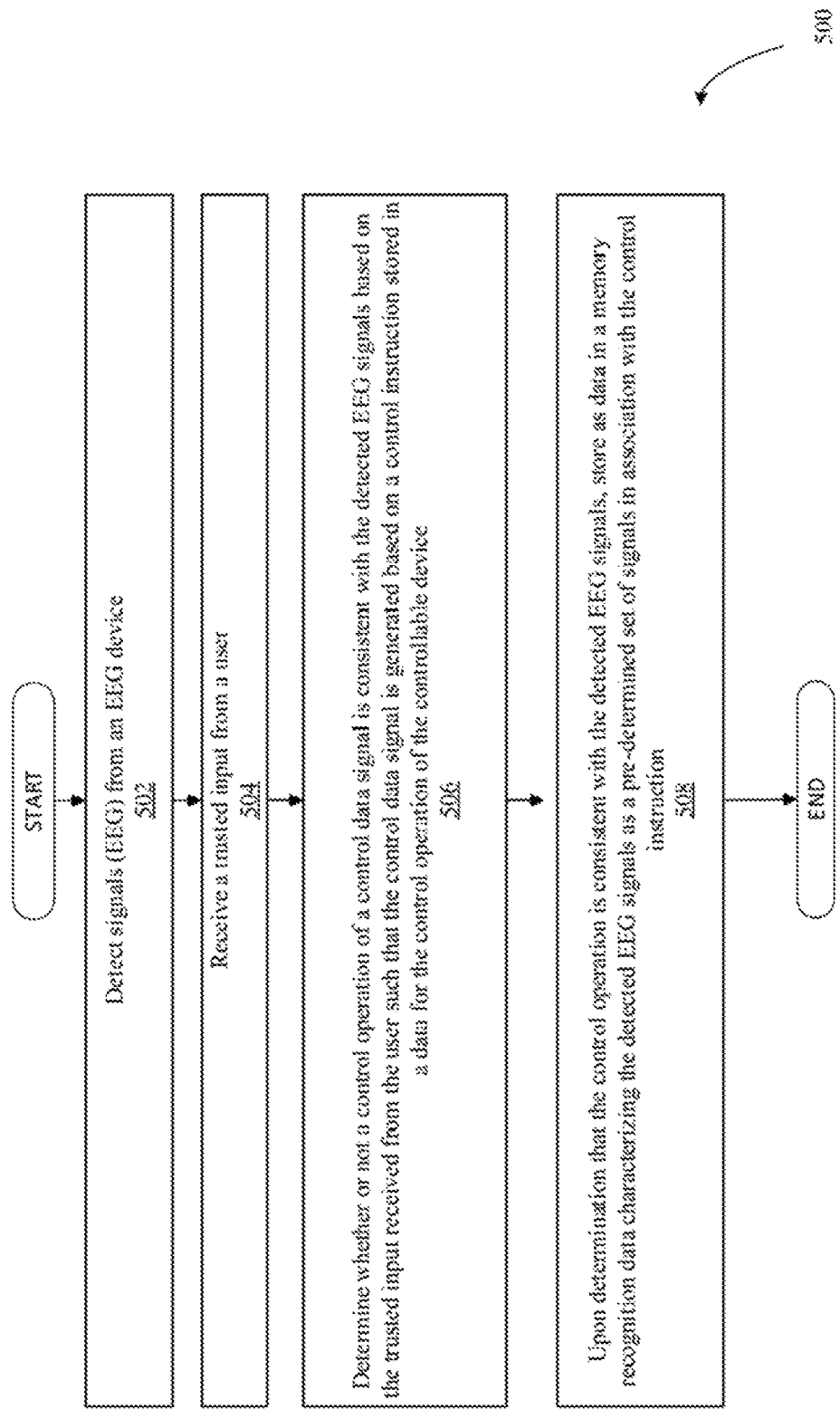
FIG. 5A is an example flowchart illustrating a method for system level training of an EEG based system for controlling a premises related service provided by a controllable device in an area of a premises.

FIG. 5A illustrates an example of a flowchart of a method 500 for system level training of an EEG based system (see FIG. 1) for controlling a premises related service in an area 101 of a premises. In one implementation, the method 500 is performed by the processor 110 of FIG. 1.

At block 502, detect signals (EEG signals) from an EEG device. In one implementation, the EEG signals are detected in an area including a premises related service provided by a controllable device. In one implementation, the controllable device includes one of a luminaire or a building automation control (BAC) appliance. As discussed above, in one implementation, the EEG device is configured to be positioned on a head of a user and the real-time detected signals are signals detected from a brain of the user. At block 504, receive a trusted input from a user. In one example, the user is a user of the EEG device. At block 506, determine whether or not a control operation of a control data signal is consistent with the detected EEG signals based on the trusted input received from the user such that a control data signal is generated based on a control instruction stored in a data for the control operation of the controllable device. In one implementation, the control instruction is associated with controlling the premises related service provided by the luminaire or the BAC appliance. As discussed above, in one implementation, one of the luminaire or the BAC appliance is selected based on the control instruction and the associated control data signal is generated for the selected one of the luminaire or the BAC appliance. At block 508 upon determination that the control operation is consistent with the detected EEG signals, store in a memory, recognition data characterizing the detected EEG signals as a pre-determined set of signals in association with the control instruction.

Figure 5B:
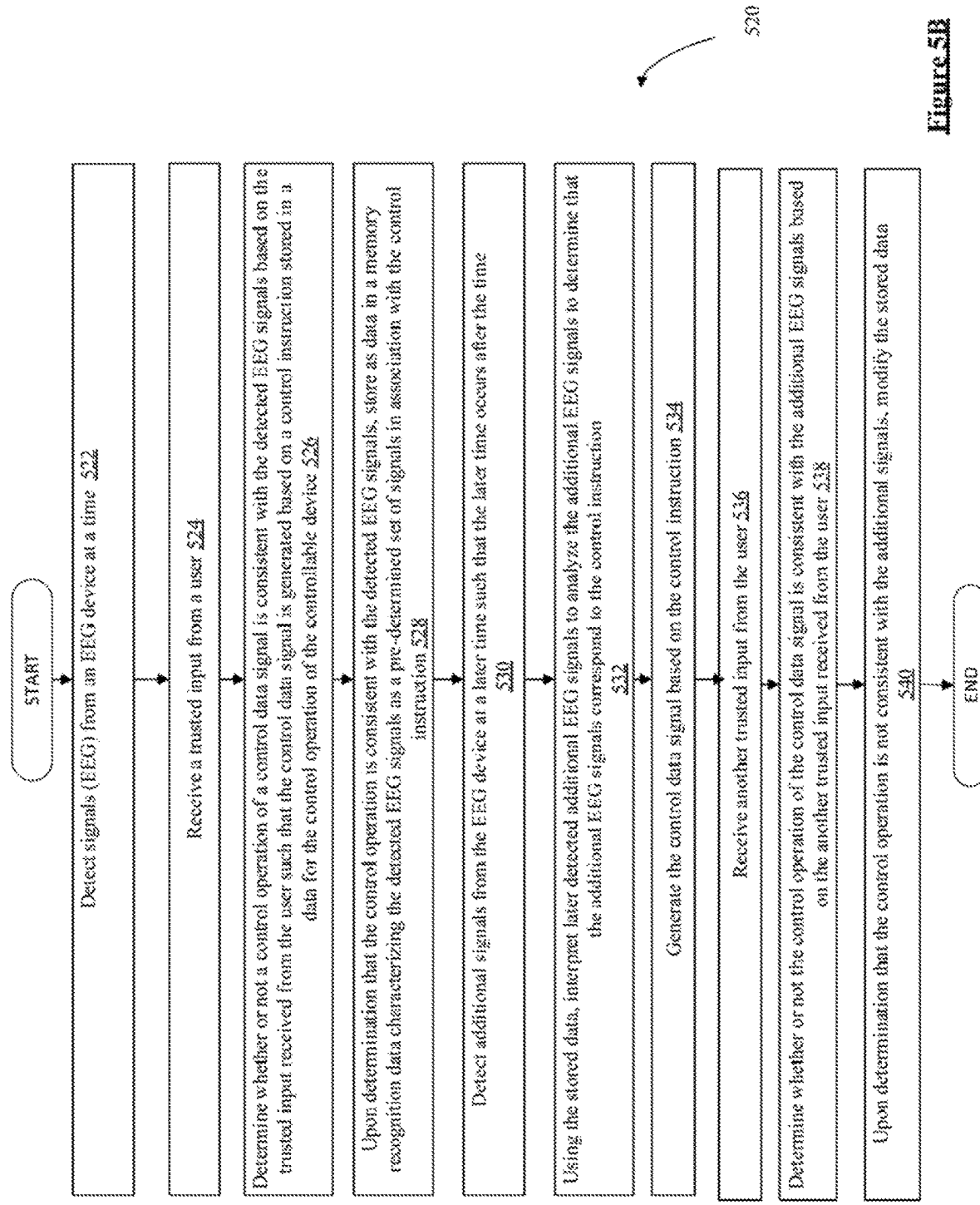
FIG. 5B is another example flowchart illustrating a method for system level training of an EEG based control system.

FIG. 5B illustrates an example of a flowchart of a method 520 for system level training of an EEG based system (see FIG. 1) for controlling a premises related service in an area 101 of a premises. In one implementation, the method is performed by the processor 110 of FIG. 1.

At block 522, detect signals from an EEG device at a time. In one implementation, the EEG signals are detected in an area including a premises related service provided by a controllable device at a time. At block 524, receive a trusted input from a user. At block 526, determine whether or not a control operation of a control data signal is consistent with the detected EEG signals based on the trusted input from the trusted input received from the user such that the control data signal is generated based on a control instruction stored in a data for the control operation of the controllable device. At block 528 upon determination that the control operation is consistent with the detected EEG signals, store, in a memory, recognition data characterizing the detected EEG signals as a pre-determined set of signals in association with the control instruction.

At block 530, detect additional signals from the EEG device at a later time such that the later time occurs after the time. At block 532, using the recognition data, interpret later detected additional EEG signals to analyze the additional EEG signals to determine that the additional EEG signals correspond to the control instruction. At block 534, generate the control data signal based on the control instruction. At block 536, receive another trusted input from the user. At block 538, determine whether or not the control operation of the control data signal is consistent with the additional EEG signals based on another trusted input received from the user. At block 540, upon determination that the control operation is not consistent with the additional signals, modify the recognition data. In one implementation, modify the recognition data based on characterizing data derived from the additional EEG signals. In one implementation, identify another control instruction and store in the memory, recognition data characterizing the additional EEG signals as another predetermined set of signals, in associated with another control instruction.

Figure 5C:
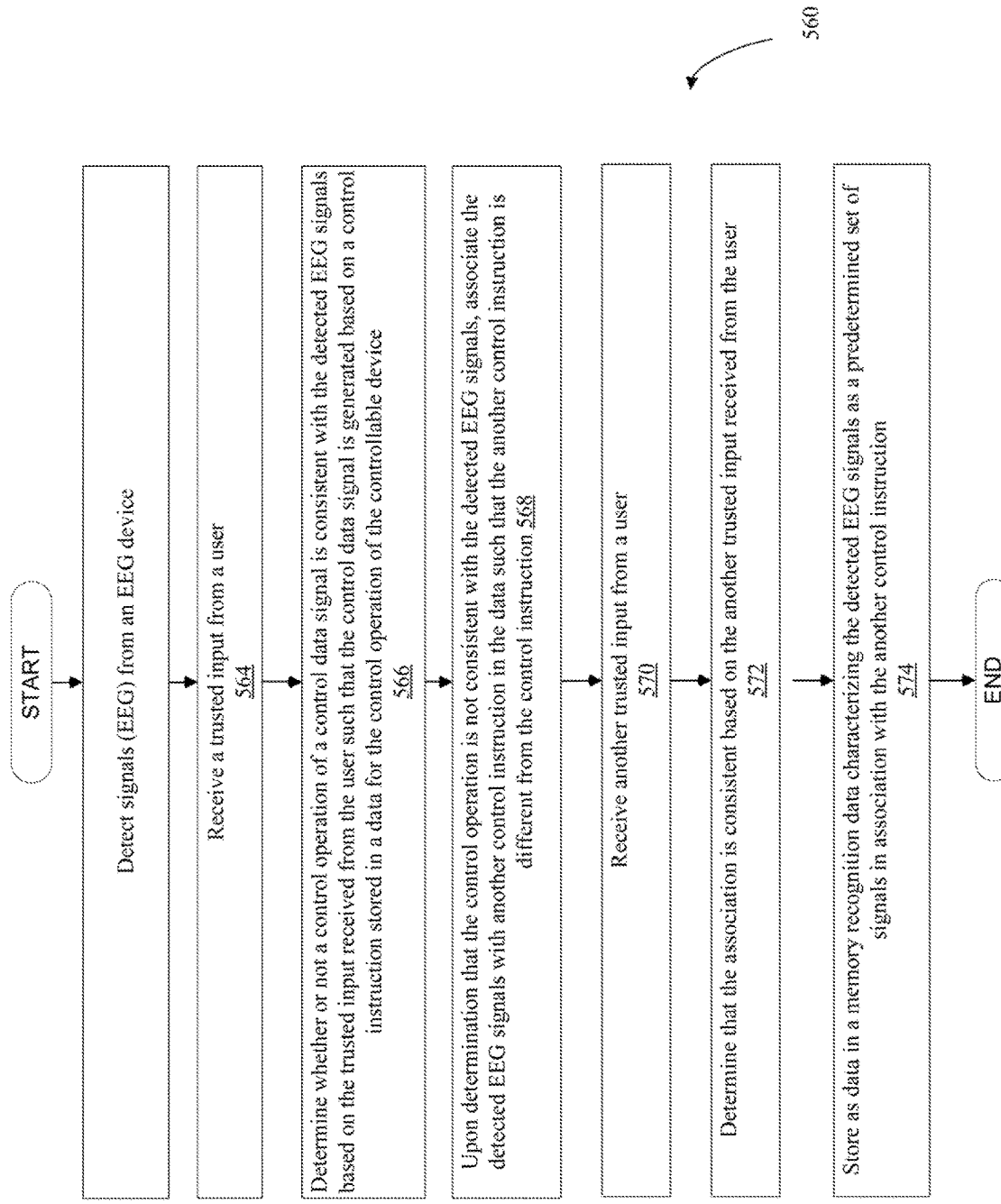
FIG. 5C is a further example flowchart illustrating a method for system level training of an EEG based control system.

FIG. 5C illustrates an example of a flowchart of a method 560 for system level training of an EEG based system (see FIG. 1) for controlling a premises related service in an area 101 of a premises. In one implementation, the method is performed by the processor 110 of FIG. 1.

At block 562, detected signals (EEG signals) from an EEG device. In one implementation, the EEG signals are detected in an area including a premises related service provided by a controllable device. At block 564, receive a trusted input from a user. At block 566, determine whether or not a control operation of a control data signal is consistent with the detected EEG signals based on the trusted input received from the user such that the control data signal is generated based on a control instruction stored in a data for the control operation of the controllable device. At block 568, upon determination that the control operation is not consistent with the detected signals, associate the detected EEG signals with another control instruction in the data such that another control instruction is different from the control instruction. At block 570, receive another trusted input from the user. At block 572, determine that the association is consistent based on another trusted input received from the user. At block 574, store, in a memory, a recognition data characterizing the detected EEG signals as a predetermined set of signals in association with another control instruction. In one implementation, associate the detected EEG signals with another control instruction in the data. In another implementation, generate, based on another control instruction, another control data signal for control of the operation of the controllable device.

Figure 6:
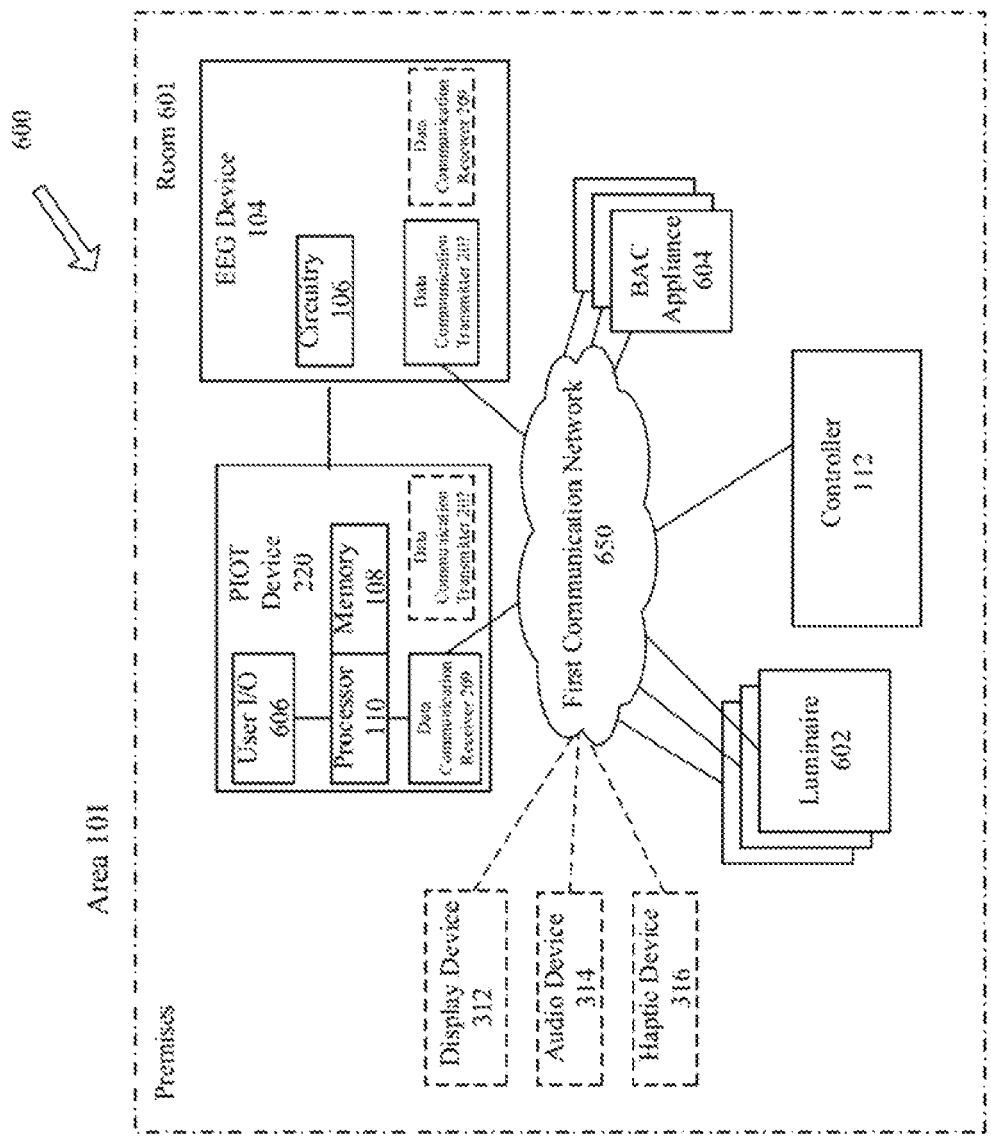
FIG. 6 is a functional block diagram of an example of a system of lighting related equipment and building automation control (BAC) capable appliances as well as one or more computer elements that may offer training of EEG control of the lighting related equipment and the BAC capable appliance.

As discussed above, the controllable device 102 provides a premises related service in an area 101 of a premises. The controllable device 102 may include luminaire, various BAC appliances etc. FIG. 6 illustrates an example of a system 600 that offers training of EEG control of the light related equipment and the BAC capable appliance serving an area 101 of the premises represented by a room 601. The room 601 includes a luminaire 602 and a BAC appliance 604 both of which represent the controllable device 102. The luminaire 602 is configured to provide a desired level of lighting for the intended use of the particular space in the room 601 and the BAC appliance 604 is configured for instance, regulate the temperature in the room 601 or control access to the room 601, etc. Although, FIG. 6 illustrates providing lighting control and building management services in the room 601, it is known to one of ordinary skill in the art that such services are provided in a similar manner in other rooms and/or other types of services areas within or on a particular area of the premises such as in a building or indoors and outdoors about a campus or the like. Also, even though, a single luminaire and a single BAC appliance is illustrated in the room 601, one of ordinary skill in the art would appreciate that the room 601 may include multiple luminaires and multiple BAC appliances.

In one implementation, the room 601 includes the controller 112 as a separate standalone system component, although, the controller 112 may be included in the luminaire 602 and the BAC appliance 604. The controller 112 is configured to control the premises related services in the room 601. In one implementation such premises related services include lighting operations, of the system such as occupancy, ambient light level or color characteristics of light in the area or level or color of light emitted from the luminaire 602 serving the particular portion of the area. In another implementation, such premise related services include operations relevant to building management functions of the system or for more general communication about conditions in the area for still further purposes. Examples of other operations include temperature or humidity for HVAC control, vibration for reporting of earthquakes or similar events, fire, smoke or gas detection, sound for user input or for detection of breakage or the like, as well as window or door state for security or access control. Other examples of operations include power monitoring, an object/occupant identification, etc.

In one implementation, the controller 112 is coupled to communicate with the controllable device 102 such as the luminaire 602 and the BAC appliance 604 via a first communication network 650 such as optical, radio frequency wireless or wired communication. In one example, the premises related service is the light related operations. The controller 112 is configured to control the light related operations associated with the luminaire 602. In another example, the premises related service is the building management functions. In another example, the controller 112 is configured to control the building management functions associated with the BAC appliance 604. In one implementation, a user (not shown) with EEG device 104 including the circuitry 106 and the data communication transmitter 207 is configured to be positioned on a head of the user is in the room 601. In one example, the EEG device 104 detects EEG signals from the brain of the user, which are processed by the circuitry 106 and transmitted by the data communication transmitter 207 to the PIOT device 220 of the user. The EEG device 104 may also include the data communication receiver 209 as shown. The PIOT device 220 may also include the data communication transmitter as shown. In one implementation, the EEG device 104 and the PIOT device 220 communicate with each other via the first communication network 650. In an alternate implementation, the EEG device 104 and the PIOT device 220 directly communicate with each other, for example, via a wire or fiber link. In another alternate implementation, the PIOT device 220 is coupled to communicate with one or more of the user devices (e.g. display device 312, audio device 314 and haptic device 316).

In one implementation, as discussed above during the training phase, the processor 110 utilizes the instructions in the memory 108 to execute functions such as determine whether or not the control operation of the control data signal is consistent with the detected EEG signals based on the trusted input from the user and upon determination that the control operation is consistent with the detected EEG signals, store in the memory 108, recognition data characterizing the detected EEG signals as predetermined set of signals in association with the control instruction. In another implementation, the processor 110 utilizes the program instructions in the memory 108 to generate a control data signal based on the control instruction. The data communication receiver 209 transmits the control data signal to the controller 112 to control the premises related service provided by one of the luminaire 602 and/or the BAC appliance 604 in the room 601. Also, as discussed above, during the training phase, upon determination that the control operation is not consistent with the detected EEG signals, the processor 110 associates the detected EEG signals with another control instruction in the data, determines that the association is consistent upon another trusted input from the user and stores in the memory 108, recognition data characterizing the detected signals s pre-determined set of signals in association with another control instruction. In another implementation, the processor 110 utilizes the program instructions in the memory 108 to generate another control data signal based on another control instruction. The data communication receiver 209 transmits another control data signal to the controller 112 to control the premises related service provided by one of the luminaire 602 and/or the BAC appliance 604 in the room 601. In one example, the EEG device 104 and the PIOT device 220 includes a user interface (UI) 606 to communicate with the user device such as the display device 312, audio device 314 and haptic device 316. Some examples of the UI 606 includes toggle switch, one or more push button switches, a rotary controller, one or more sliders, a keypad, various indicator lights, haptic feedback components, and/or a touchscreen display. Other examples of the UI may include a video input and associated processing for gestural control detection, a microphone, an occupancy/motion sensor, proximity sensor, etc. Although not shown, each of the system elements that uses power to operate as described will include a power supply circuit and will connect to or possibly contain a power source.

Although the EEG device, PIOT device and any optional output devices for providing feedback or other information to the user may be separated, in most examples, such devices will be carried or worn by the user at any one time, whether on or off of the premises where the controllable device is located.

Figure 6A:
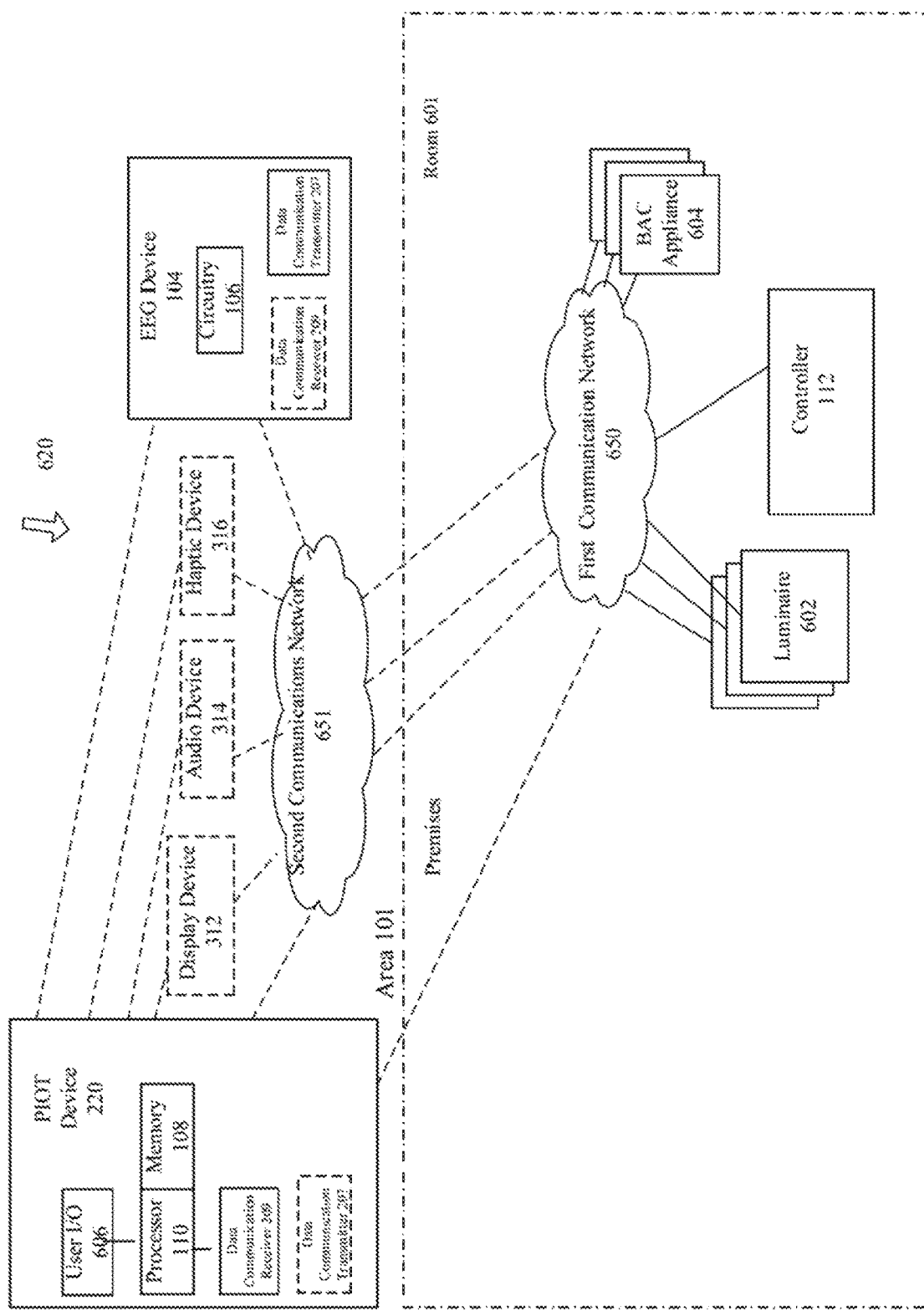
FIG. 6A is a functional block diagram of another example of lighting related equipment and building automation control (BAC) capable appliances as well as one or more computer elements that may offer training of EEG control of the lighting related equipment and the BAC capable appliance.

FIG. 6A illustrates another example of a system 620 serving the area 101 of the premises represented by the room 601. The system 620 functions similar to the system 600 discussed above except the EEG device 104 and the PIOT device 220 are located outside the area 101 such that the EEG signals are detected by the EEG device 104 outside of the premises of the room 601, which are then processed by the circuitry 106 and transmitted by the data communication transmitter 207 to the PIOT device 220. The PIOT device 220 is shown by way of example outside of the premises and/or possibly outside of the room 601, e.g. where the EEG device 104 and the PIOT device 220 are worn and/or carried by the user. The PIOT device 220, however, may be inside the room and/or the premises (e.g. at the same or another location as the EEG device 104). In one example, the user devices such as the display device 312, audio device 314 and haptic device 316 are also located outside the premises of the room 601, e.g. with the user wearing the EEG device 104; and the EEG device 104 and the PIOT device 220 device communicate with each other and with such user devices via a second communication network 651 such as an optical, RF wireless or a wired communication network.

Figure 6B:
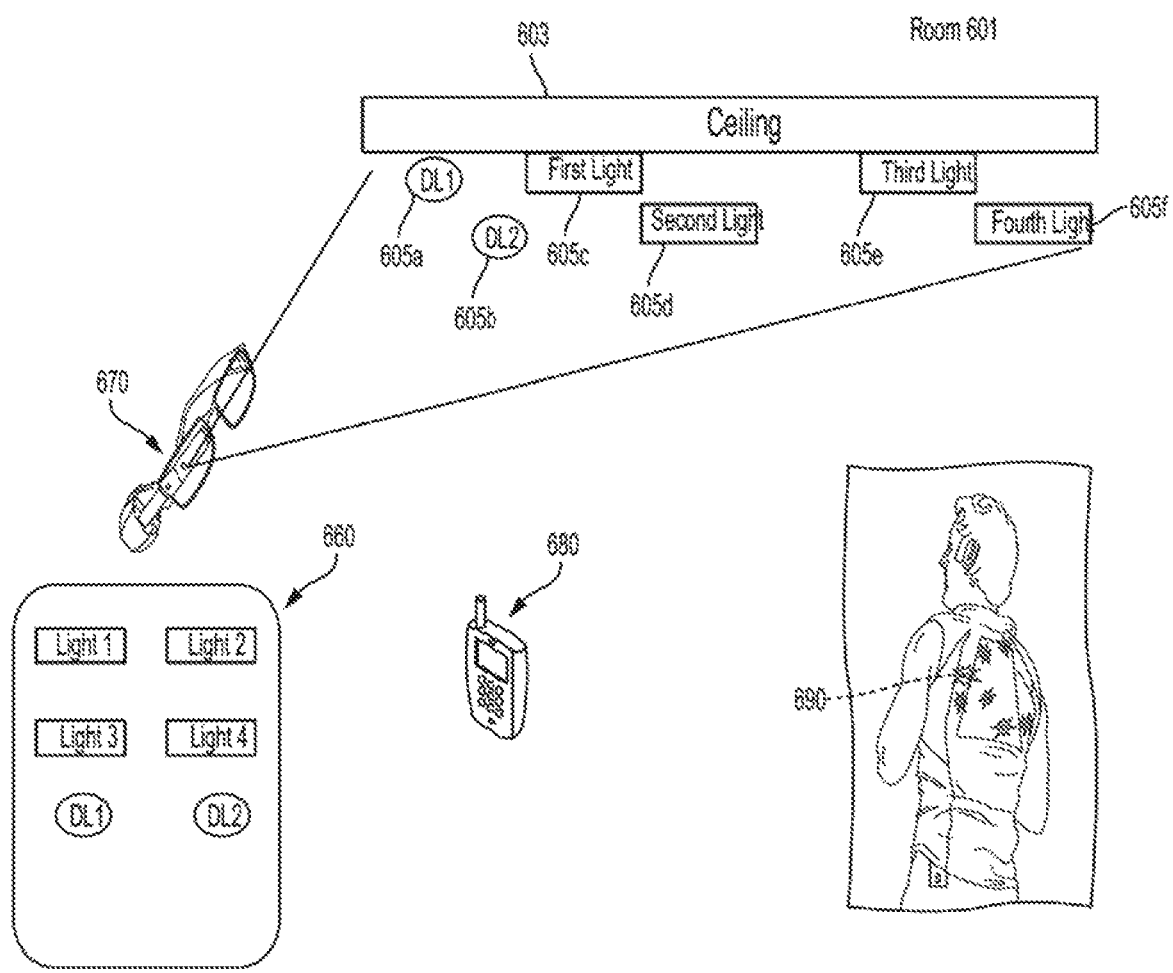
FIG. 6B illustrates an example of providing data associated with the lighting devices in the area.

FIG. 6B illustrates an example of providing data associated with the lighting device as the controllable device 102 in the room 601. Also, shown is a ceiling 603 in the room 601 luminaires or the like labeled as "lights" for convenience in the drawing. In one example, there are illustrated six lighting devices, two downlights, a first ($1^{st}$) downlight (DL1) 605a a second ($2^{nd}$) downlight (DL2). 605b, and four lights, a first light 605c, a second light 605d, a third light 605e, and a fourth light 605f. In one example, the four lights 605c-605f are mounted on or hung below the ceiling 603. In one example, the two downlights, 605a and 605b are downlight type fixtures that may be recessed into, mounted or hung below the ceiling 603. Although the light sources are illustrated to be located on the ceiling 603, it should be apparent that the light sources may be located either wall or floor or combinations thereof in the room 601. Also, in the example, six lighting devices are shown, it is known to one of ordinary skill in the art that less than or more than six lighting devices may be provided in the room 601. The lighting devices may include but not limited to light emitting diodes (LEDs), fluorescent lamps, halogen lamps, metal halide lamps, high intensity discharge lamps or like.

In one implementation, the data associated with the six lighting devices is provided to the user via one of the user devices such as the display device 312, audio device 314 and the haptic device 316. In one example the data is provided to the user upon request from the user when the user enters the room 601. In another example, the data is automatically provided to the user when the user enters the room 601. In one example, the display device 312 is a smartphone 660 and the data may be displayed on a screen of the smartphone 660 as shown. In another example, the display device is a head gear 670 including a camera (not shown) and the data may be displayed to the user who wears the head gear 313. In one example, the head gear 670 are augmented reality (AR) glasses, which includes additional hardware such as an optical sensor/camera (not shown) to track the eyeball of the wearer of the AR glasses and estimates gaze so that EEG commands to control the lights can be directed to specific lights being looked at by the wearer of the AR glasses. Other administrator level functions such as grouping lights can also be performed, highly augmented by the visual feedback to the AR glasses. In one example, the audio device 314 is a standard phone 680 and the data is provided to the user via audio on the standard phone 680. In one example, the haptic device 316 is a wearable device 690, which provides for a physical contact between the user and a computer such as the user will receive the data via felt sensation on some part of the body. In one example, upon user selection of the data (associated with the lighting devices as shown) as provided to the user, user selections are collected and stored as the user preference data. As discussed above, the user preference data is preferred user selection of one or more control operations among the identified control operations of the controllable device 102 supported by the controllable 112.

Figure 7:
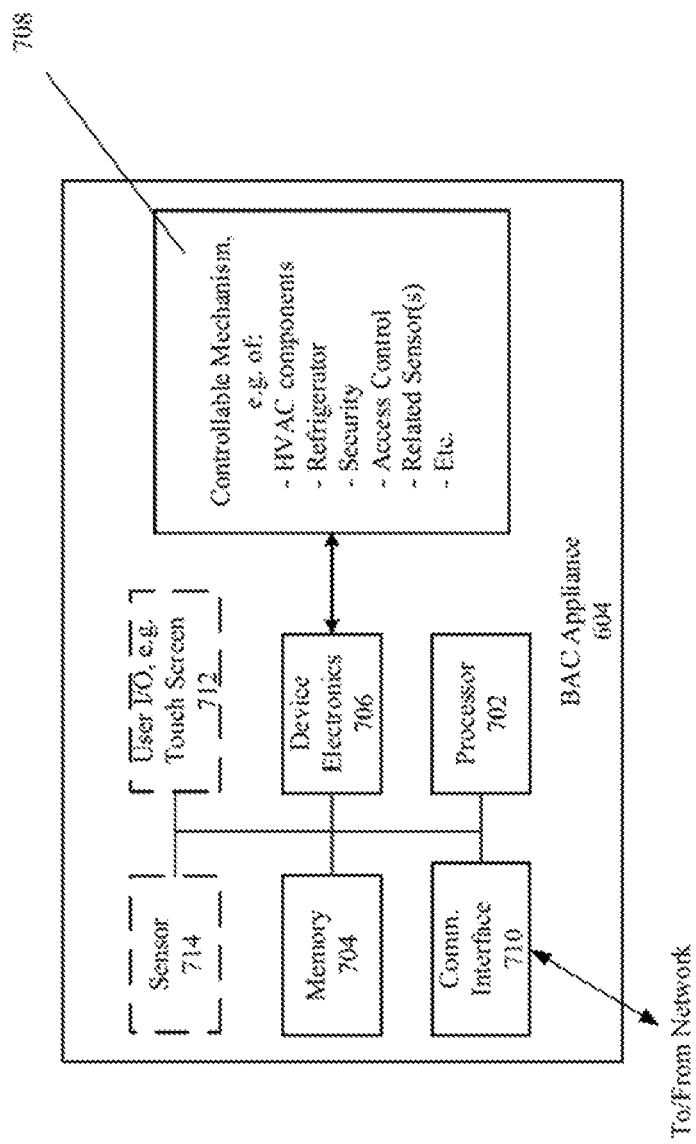
FIG. 7 is a functional block diagram of an example of an intelligent building automation control (BAC) capable appliance of FIG. 6.

FIG. 7 illustrates functional block diagram of an example of an intelligent building management element, such as the BAC appliances 604 shown in FIG. 6. The BAC appliance 604 is an intelligent device in that the BAC appliance 604 includes a processor 702 and a memory 704 and program in the memory 704 for execution by the processor 702 to implement the intended functions of the BAC appliance 604. This 'brain' of the BAC appliance 604 will be coupled to and control appropriate device drive electronics 706. The drive electronics 706 provides an interface to a controllable mechanism 708 of the particular BAC appliance 604, to allow the processor 702 to control the mechanism, or to receive sensor data from the mechanism or both. The drive electronics 706 and the programming (e.g. stored in memory 704) that is run by the processor 702 to control operation of each particular BAC appliance 604 will depend on the particular type device used as the mechanism 708 and thus on the particular type of building management BAC appliance product it represents or implements.

The examples of BAC appliance 604 may be virtually any type of device, which may utilize data communications, in this case, via the elements and network of the system 600 of FIG. 6. By way of a few examples, the controllable mechanism 708 may be any of a variety of HVAC components (e.g. elements of a thermostat, one or more elements of the heat/cooling system, controllable vents or dampers within the duct work), one or more cooling or other elements of a refrigerator, any of a variety of components of a security system, any of a variety of access control elements, and/or sensors related to any or all of the above functions. The BAC appliance 604 also includes a communication interface 710. Similar to the communication interfaces in the other intelligent system elements (FIG. 6), the interface 710 connects or otherwise couples to the network in the service area and supports two-way data communication through the first communication network 650.

In the example of FIG. 7, although the BAC appliance 604 is shown as having one processor 702, it is known to one of ordinary skill in the art that the BAC appliance 604 may include multiple processors. For example, a particular configuration for a BAC appliance 604 may utilize a multi-core processor architecture. Also, some of the other components, such as the communications interfaces, may themselves include processors. Alternatively, the BAC appliance 604 may use a Micro-Control Unit (MCU), which is a microchip device (e.g. small computer or computer like device formed on a single chip) that incorporates a processor serving as the programmable central processing unit (CPU) as well as one or more of memories 704.

The BAC appliance 604 may include one or more input and/or output (I/O) elements 712 for a user interface (instead of or in addition to the mechanism 708). The user I/O element 712, for example, may include a toggle switch, a rotary controller, one or more sliders, a keypad and/or a touchscreen display. The precise user I/O element, if provided, depends on the operational characteristics of the particular BAC appliance 604. For example, for an HVAC controller, the user I/O element(s) 712 might be similar to those of a digital thermostat. A touchscreen display, as another example, may support touch and touch gesture input as well as visual display output. Other examples of the UI input may include a video input and associated processing for gestural control detection, a microphone, an occupancy/motion sensor, proximity sensor, etc. If provided, outputs may be visual, audible, tactile, etc. For example, a microphone and/or speaker may be used to support audible input and/or output, whereas a camera in combination with projector or display may be used to support visual input and/or output.

As an alternative or in addition to any sensors included in the controllable mechanism 708, the BAC appliance 604 may include one or more sensors 714 (instead of or in addition to the mechanism 401). If included, the type of sensor in a particular BAC appliance 604 would depend on the type of element and/or the mechanism 708 that the 'brain' controls either within the appliance itself or in same or another appliance via a BMS application 727 stored in the memory 704.

Figure 8:
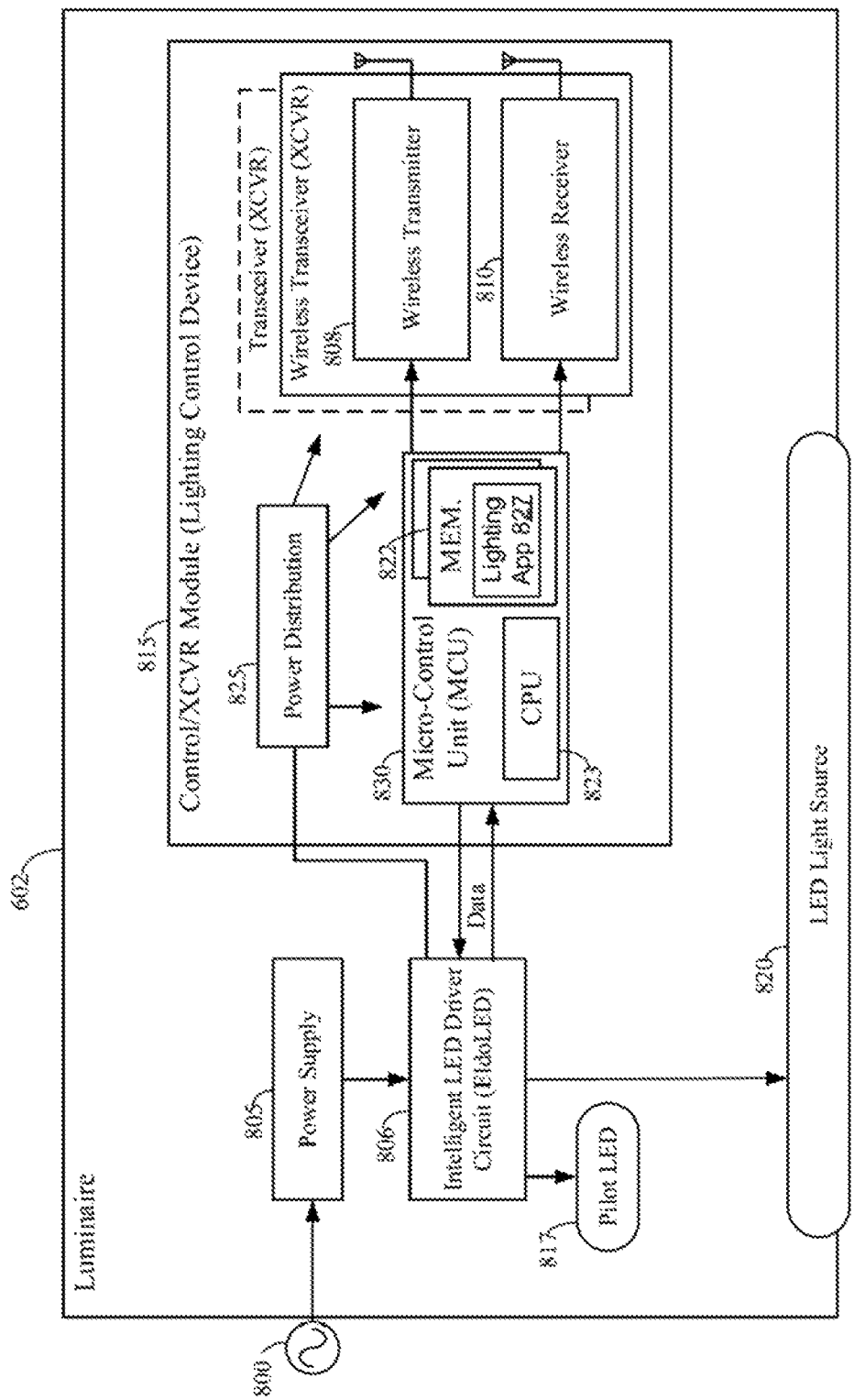
FIG. 8 is a functional block diagram of an example of an intelligent luminaire of FIG. 6.

FIG. 8 illustrates a block diagram of an example of an intelligent luminaire, such as the luminaire 602 as shown in FIG. 6. Luminaire 602 is an integrated light fixture that generally includes a power supply 805 driven by a power source 800. Power supply 805 receives power from the power source 800, such as an AC mains, battery, solar panel, or any other AC or DC source. Power supply 805 may include a magnetic transformer, electronic transformer, switching converter, rectifier, or any other similar type of circuit to convert an input power signal into a power signal suitable for luminaire 602.

Luminaire 602 furthers include an intelligent LED driver circuit 806, control/XCVR module 815, and a light emitting diode (LED) light source 820. Intelligent LED driver circuit 806 is coupled to LED light source 820 and drives that LED light source 820 by regulating the power to LED light source 820 by providing a constant quantity or power to LED light source 320 as its electrical properties change with temperature, for example. The intelligent LED driver circuit 806 includes a driver circuit that provides power to LED light source 820 and a pilot LED 817. The pilot LED 817 may be included as part of the control/XCVR module 315. Intelligent LED driver circuit 806 may be a constant-voltage driver, constant-current driver, or AC LED driver type circuit that provides dimming through a pulse width modulation circuit and may have many channels for separate control of different LEDs or LED arrays. An example of a commercially available intelligent LED driver circuit 806 is manufactured by EldoLED. LED driver circuit 806 can further include an AC or DC current source or voltage source, a regulator, an amplifier (such as a linear amplifier or switching amplifier), a buck, boost, or buck/boost converter, or any other similar type of circuit or component. LED driver circuit 806 outputs a variable voltage or current to the LED light source 820 that may include a DC offset, such that its average value is nonzero, and/or an AC voltage.

Control/XCR module 815 includes power distribution circuitry 825 and a micro-control unit (MCU) 830. As shown, MCU 830 is coupled to LED driver circuit 806 and controls the light source operation of the LED light source 820. MCU 830 includes a memory 322 (volatile and non-volatile) and a central processing unit (CPU) 823. The memory 822 includes a lighting application 827 (which can be firmware) for both occupancy sensing/counting and lighting control operations. The power distribution circuitry 825 distributes power and ground voltages to the MCU 830, wireless transmitter 808 and wireless receiver 810, to provide reliable operation of the various circuitry on the sensor/processing circuitry chip.

Luminaire 602 also includes a wireless radio communication interface system configured for two way wireless communication on at least one band. Optionally, the wireless radio communication interface system may be a dual-band system. It should be understood that "dual-band" means communications over two separate RF bands. The communication over the two separate RF bands can occur simultaneously (concurrently); however, it should be understood that the communication over the two separate RF bands may not actually occur simultaneously.

In our example, the luminaire 602 has a radio set that includes radio transmitter 808 as well as a radio receiver 810, together forming a radio transceiver. The wireless transmitter 808 transmits RF signals on the lighting network. This wireless transmitter 808 wireless communication of control and systems operations information, during luminaire operation and during transmission over the first wireless communication band. The wireless receiver carries out receiving of the RF signals from other system elements on the network and generating RSSI data based on signal strengths of the received RF signals. If provided (optional) another transceiver (Tx and Rx) may be provided, for example, for point-to-point communication, over a second different wireless communication bands, e.g. for communication of information other than the control and systems operations information, concurrently with at least some communications over the first wireless communication band. Optionally, the luminaire 602 may have a radio set forming a second transceiver (shown in dotted lines, transmitter and receiver not separately shown). The included transceiver (solid lines), for example, may be a sub GHz transceiver or a Bluetooth transceiver configured to operate in a standard GHz band. A dual-band implementation might include two transceivers for different bands, e.g. for a sub GHz band and a GHz band for Bluetooth or the like. Additional transceivers may be provided. The particular bands/transceivers are described here by way of non-limiting example, only. If two bands are supported, the two bands may be for different applications, e.g. lighting system operational communications and system element maintenance/commissioning. Alternatively, the two bands may support traffic segregation, e.g. one band may be allocated to communications of the entity owning/operating the system at the premises whereas the other band may be allocated to communications of a different entity such as the system manufacturer or a maintenance service bureau.

The MCU 830 may be a system on a chip. Alternatively, a system on a chip may include the transmitter 808 and receiver 810 as well as the circuitry of the MCU 830. As shown, the MCU 830 includes programming in the memory 822. A portion of the programming configures the CPU (processor) 823 to control light source and/or determine occupancy sensing/counting in an area in the lighting network, including the communications over one or more wireless communication. The programming in the memory 822 includes a real-time operating system (RTOS) and further includes a lighting application 827 which is firmware/software that engages in communications with controlling of the light source, for example, controlling the light source based on occupancy sensing/counting determined by the CPU 823. The lighting application 827 programming in the memory 822 carries out lighting control operations in the area. The programming for the determination of an occupancy and/or occupancy count in the area and/or lighting control may be implemented as part of the RTOS, as part of the lighting application 827, as a standalone application program, or as other instructions in the memory.

As shown by the above discussion, functions relating to the EEG training to control the luminaire and building management appliances may be implemented on computers connected for data communication via the components of a wireless communication network, operating as one or more network connected hardware elements in the wireless communication network as shown in FIG. 6. Although special purpose devices may be used, such devices also may be implemented using one or more hardware platforms intended to represent a general class of data processing device, albeit with an appropriate network connection for data communication.

As known in the data processing and communications arts, a general-purpose computer typically comprises a central processor or other processing device, an internal communication bus, various types of memory or storage media (RAM, ROM, EEPROM, cache memory, disk drives etc.) for code and data storage, and one or more network interface cards or ports for communication purposes. The lighting control and building management control functionalities involve programming, including executable code of the software architecture, as well as associated stored data, e.g. the files or other data used or processed during execution of the software architecture. The software code is executable by the general-purpose computer that functions as an actual or physical gateway device and/or one or more general-purpose computers that implement the gateway functions in the cloud. In operation, the code is stored within the general-purpose computer platform. At other times, however, the software architecture and/or any associated files or other data may be stored at other locations and/or transported for loading into the appropriate general-purpose computer system. Execution of such code by a processor of the computer platform enables the platform to implement the methodology or functionalities for the implementation of EEG training for controlling of the luminaire and the building management appliance, in essentially the manner performed in the implementations discussed and illustrated herein.

Figure 9:
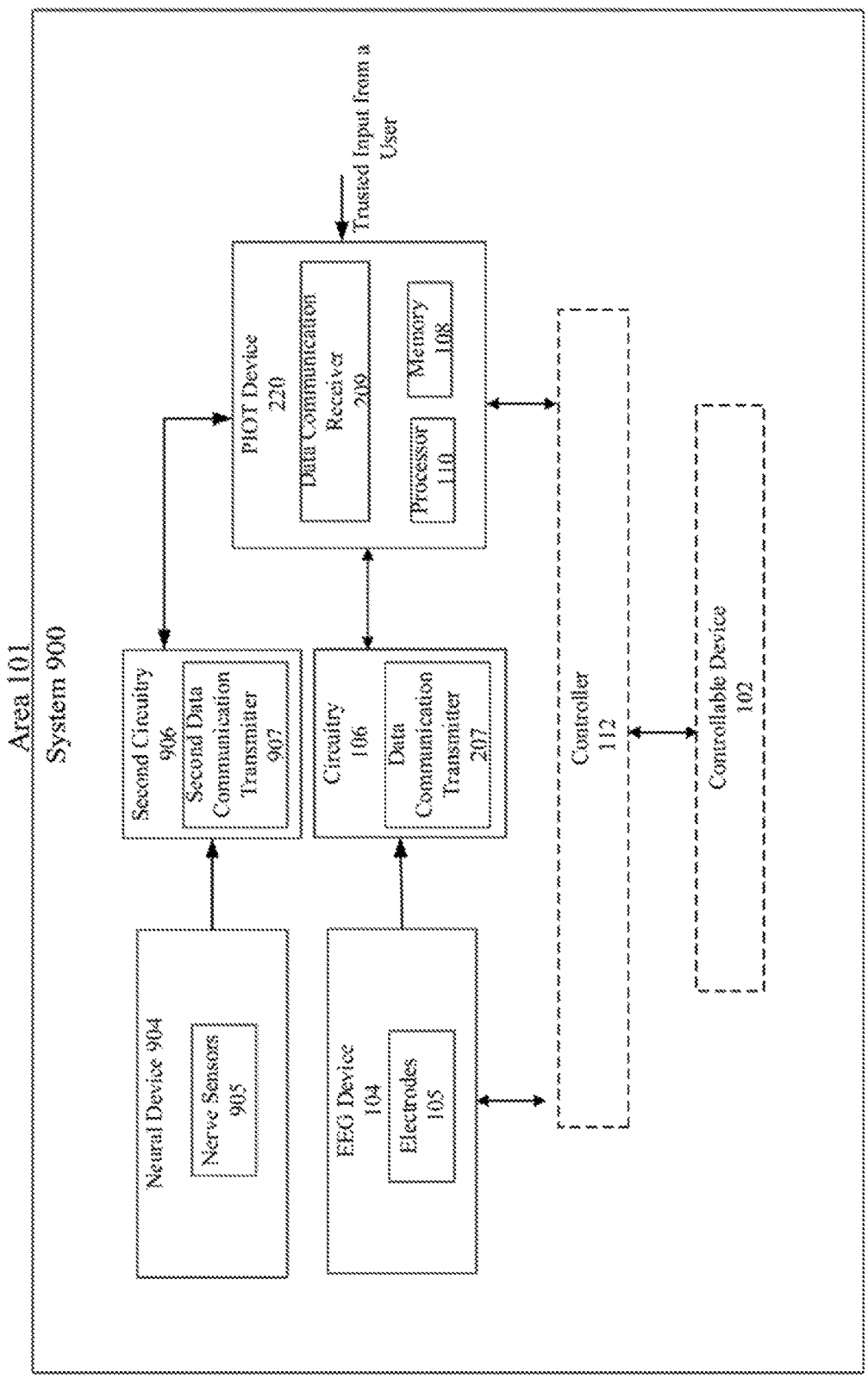
FIG. 9 illustrates another example of a system for training equipment for an EEG based and neuro based control of a premises related service provided by a controllable device in an area of a premises.

FIG. 9 illustrates an example of a system 900, which includes the same components as system 200 as described with respect to FIG. 2 and further includes a neural device 904 coupled to a second circuitry 906. In one example, the neural device 904 is configured to be positioned on some part of the human body, for example, as a glove to be worn on a person's hand or as a cuff to be worn on person's wrist or forearm. In another example, the neural device 904 is a neural sensor implanted inside the user's body. In one implementation, the neural device 904 includes one or more nerve sensors 905 configured to detect nerve signals from a nervous system of the part of the body such as finger, back, hand, forearm etc. on which the neural device 904 is positioned. In one implementation, as discussed above the memory 108 stores a data including a plurality of control instructions. In one example, a person may have neural device 904 positioned on the person's hand and an user input is a person moves his/her hand such that when the person moves his/her hand, the signals from the nerves of the person's hand are detected. In one example, the user identification data is uniquely associated with the neural sensor device 904 identifying a user among a plurality of users of the neural device 904 in the area 101 of the premises. The user's location is tracked based on the user identification data associated with one or more of the EEG device 104, neural device 904 and the PIOT device 220.

In one implementation, as discussed above, the processor 110 generates, based on a control instruction among the plurality of instructions stored in the memory 108, a control data signal for control of an operation of a controllable device 102, which is configured to provide a premises related serve in the area 101. In one example, the second circuitry 906 processes the nerve signals received from the one or more nerve sensors 905 of the neural device. The second circuitry 906 also includes a second data communication transmitter 907, which functions to transmit the processed nerve signals to the PIOT device 220. In one implementation, the processor 110 processes the nerve signals similar to the processing of the signals detected by the electrodes 105 of the EEG device 104 as discussed with respect to FIG. 1.

In one implementation, the processor 110 is coupled to the circuitry 106 and thus during the training phase, configures the neural device 904 to receive data regarding the detected nerve signals and determines whether or not the control operation of the control data signal is also consistent with the detected nerve signals based on a first trusted input received from the user. In one implementation, upon determination that control operation of the control data signal is also consistent with the detected nerve signals, the processor 110 functions to store the recognition data characterizing the detected nerve signals as another pre-determined set of signals in association with the control instruction. In one implementation, the processor 110 functions to associate the detected nerve signals with the control instruction in the data. In one implementation, the neural device 904 detects additional nerve signals at a later time after the detection of the nerve signals. In one example, the later time is during training phase. In another example, the additional the later time is during real-time operational phase. In one implementation, the processor 110 uses the stored data to interpret the additional nerve signals. Specifically, the processor 110 analyzes the additional nerve signals to determine that the additional nerve signals correspond to the control instruction. In one implementation, the processor 110 generates the control data signal based on the control instruction and determines whether or not the control operation of the control data signal is also consistent with the additional nerve signals based on a second trusted input received from the user. Upon determination that the control operation is also not consistent with the additional nerve signals, the processor 110 modifies the recognition data characterizing the nerve signals as the pre-determined set of signals in association with the control instruction based on characterizing data derived from the additional nerve signals. In one example, the processor 110 functions to identify a first control instruction among the plurality of instructions stored in the memory 108, store the recognition data characterizing the additional nerve signals as another pre-determined set of signals in association with the control instruction.

In another implementation, upon determination that control operation of the control data signal is also not consistent with the detected nerve signals, the processor 110 functions to associate the detected nerve signals with a first control instruction among the plurality of instructions stored in the memory 108. The first control instruction is different from the control instruction. In one implementation, the processor 110 determines that the association is consistent with the first control instruction upon a third trusted input from the user and stores the recognition data characterizing the detected nerve signals as pre-determined set of signals in association with the first control instruction. In one implementation, the processor 110 associates the detected nerve signals with the second control instruction in the data. In one implementation, the processor 110 generates, based on the first control instruction, a first control data signal, for control of the operation of the controllable device 102. The first control data signal is different from the data signal.

FIG. 10 includes an example of the neural device 904 of FIG. 9. The neural device 904 includes the many components that are same as or similar to like-numbered components of the EEG device 104 as described with respect to FIG. 3 with the exception of the electrodes 105. Instead of EEG electrodes, the neural device 904 includes the nerve sensors 905. As shown, the second circuitry 906 includes an analog to digital (A/D) converter 902 and a microcontroller 903. Similar to the EEG device as discussed above, the second circuitry 906 of the neural device 904 processes the nerve signals detected by the nerve sensors 905. The signals detected by the nerve sensors 905 are analog signals. In one example, A/D converter 902 converts the analog signals into digital signals and the microcontroller 903 assembles the digital signals outputted from the A/D converter 902 into a format for a transmission to the processor 110. The processor 110 is coupled to the second circuitry 906 and thus configures the neural device 904 to receive the data regarding the detected nerve signals and processes the data, as discussed above with respect to FIG. 9, to store in the memory 108, recognition data and associate the detected nerve signals with the control instruction in the second data generate the control data signal and transmit the control data signal to the controller 112 coupled or in communication with the controllable device 102.

In one implementation, training of an EEG control based system is executed by the instructions stored in the memory of a computer element, which includes a processing power to execute the instructions in a training phase to make a determination of appropriate association of the detected EEG signals with a control instruction upon a trusted input received from the user, store recognition data characterizing the detected EEG signals and update the characterizing data.

Figure 12:
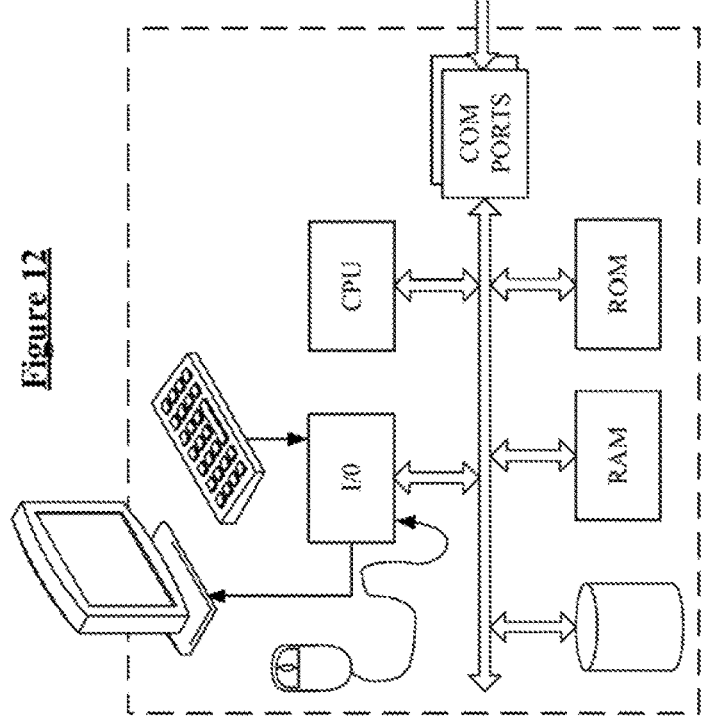
FIG. 12 is a simplified functional block diagram of a personal computer or other work station or terminal device, for possible communication with the gateway or cloud implementation of the control system.
Figure 11:
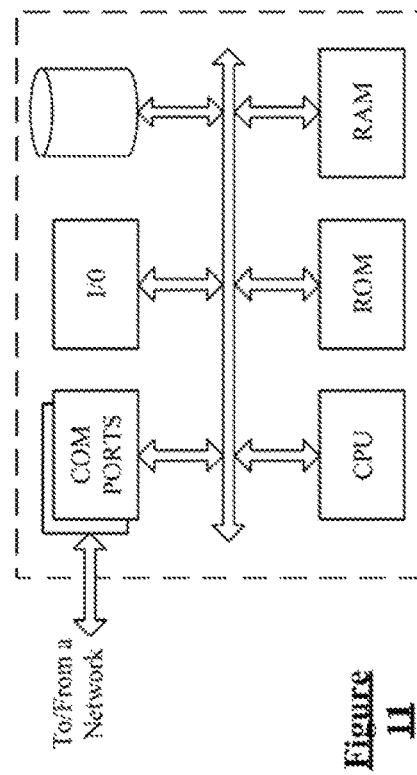
FIG. 11 is a simplified functional block diagram of a computer that may be configured as a host or server, for example, to function as the gateway or as an outside/cloud server in the control system of FIG. 1.

FIGS. 11 and 12 provide functional block diagram illustrations of general purpose computer hardware platforms. FIG. 11 illustrates a network or host computer platform, as may typically be used to implement a server, gateway or cloud computing platform. FIG. 12 depicts a computer with user interface elements, as may be used to implement a personal computer or other type of work station or terminal device, although the computer of FIG. 12 may also act as a server, gateway, host computer, etc. if appropriately programmed. It is believed that those skilled in the art are familiar with the structure, programming and general operation of such computer equipment and as a result the drawings should be self-explanatory.

A network computer, for example (FIG. 11), includes a data communication interface for packet data communication. That computer element also includes a central processing unit (CPU), in the form of one or more processors, for executing program instructions. The network computer platform typically includes an internal communication bus, program storage and data storage for various data files to be processed and/or communicated by the server or gateway functions, although the network computer element often receives programming and data via network communications. The hardware elements, operating systems and programming languages of such computers are conventional in nature, and it is presumed that those skilled in the art are adequately familiar therewith. Of course, the functions relating to the training of an EEG control based system, implemented via the software architecture, and may be implemented in a distributed fashion on a number of similar network computer hardware platforms, to distribute the processing load and/or offer the gateway functionalities as a cloud service.

Figure 13:
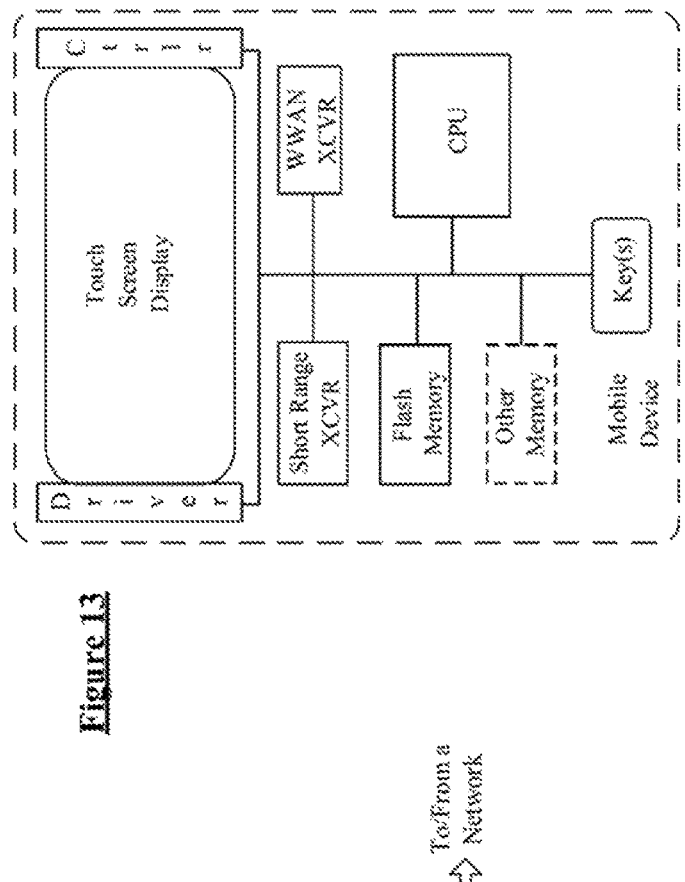
FIG. 13 is a simplified functional block diagram of a mobile device, e.g. smartphone or tablet, as an alternate example of a user terminal device, for possible communication with the gateway or cloud implementation of the control system.

A computer type user terminal device, such as a PC or tablet computer, similarly includes a data communication interface CPU, main memory and one or more mass storage devices for storing user data and the various executable programs (see FIG. 12). A mobile device type user terminal (FIG. 13) may include similar elements, but will typically use smaller components that also require less power, to facilitate implementation in a portable form factor. The various types of user terminal devices will also include various user input and output elements. A computer, for example, may include a keyboard and a cursor control/selection device such as a mouse, trackball, joystick or touchpad; and a display for visual outputs. A microphone and speaker enable audio input and output. Some smartphones include similar but smaller input and output elements. Tablets and other types of smartphones utilize touch sensitive display screens, instead of separate keyboard and cursor control elements. The hardware elements, operating systems and programming languages of such user terminal devices also are conventional in nature, and it is presumed that those skilled in the art are adequately familiar therewith.

In one implementation, the trusted input and any desired information output to the user (e.g. as to what command the system generates), during a training (only) phase might utilize a computer (see FIG. 12) or a mobile device (see FIG. 13) in communication with the PIOT device or the EEG device. Depending on processing power, the external computer or mobile device might make the determinations of appropriate associations of the detected EEG signals, tell the EEG device or the PIOT device to store in the memory, the recognition data characterizing the detected EEG signals and tell the EEG device or the PIOT device to update the characterizing data in the memory.

Hence, aspects of the functionalities for the training of EEG control based system as outlined above may be embodied in programming for the software architecture (see e.g. EEG device 104 of FIGS. 1, 2 and 3, and/or the PIOT device of FIGS. 2 and 4). Program aspects of the technology may be thought of as "products" or "articles of manufacture" typically in the form of executable code and/or associated data that is carried on or embodied in a type of machine readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of a manufacturer or control service provider into the computing element that will run the software architecture. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Program instructions may comprise a software or firmware implementation encoded in any desired language. Programming instructions, when embodied in a machine readable medium accessible to a processor of a computer system or device, render a computer system or a device into a special-purpose machine that is customized to perform the operations specified in the program instructions.

Unless otherwise stated, any and all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

While the foregoing has described what are considered to be the best mode and/or other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A system comprising:
   an electroencephalography (EEG) device configured to be positioned on a head of a user, wherein the EEG device includes one or more electrodes configured to detect EEG signals from a brain of the user;
   circuitry coupled to the one or more electrodes configured to process the EEG signals detected via the one or more electrodes of the EEG device;
   a processor coupled to or in communication with the circuitry; a memory accessible by the processor;
   program instructions stored in the memory for execution by the processor; data stored in the memory comprising a control instruction,
   wherein execution of the program instructions configures the processor to: generate, based on the control instruction, a control data signal, for control of an operation of a controllable device configured to provide a premises related service in an area of a premises; and
   wherein, in a training phase, execution of the program instructions further configures the processor to:
      determine whether or not that the control operation of the control data signal is consistent with the detected EEG signals based on a trusted input from the user, and
      upon determination that the control operation is consistent with the detected EEG signals, store, in the memory, recognition data characterizing the detected EEG signals as a predetermined set of signals in association with the control instruction.

2. The system of claim 1, wherein the execution of the program instructions configures the processor to associate the detected EEG signals with the control instruction in data in the memory.

3. The system of claim 1, wherein:
   the trusted input comprises a positive trusted input including an approval of the control operation from the user, and
   the processor is configured to utilize the positive trusted input to determine that the control operation is consistent with the detected EEG signals.

4. The system of claim 1, wherein the trusted input comprises a negative trusted input including a disapproval of the control operation of the control data signal from the user, and
   the processor is configured to utilize the negative trusted input to determine that the control operation is not consistent with the detected EEG signals.

5. The system of claim 1, wherein the trusted input comprises a positive trusted input including a user selection of the control operation, and
   the processor is configured to utilize the positive trusted input to determine that the control operation is consistent with the detected EEG signals.

6. The system of claim 1, wherein the trusted input comprises a negative trusted input including a user selection of another control operation among a plurality of control operations,
   the processor is configured to utilize the negative trusted input to determine that the control operation is not consistent with the detected EEG signals, and
   the another control operation is different from the control operation.

7. The system of claim 1, wherein the trusted input is received via a user responsive element.

8. The system of claim 1, further comprising a personal Internet of Things (PIOT) device coupled to the EEG device, wherein the circuitry includes a data communication transmitter;
   the PIOT device comprises the processor, the memory including the program instructions stored in the memory, the data stored in the memory and a data communication receiver compatible with the data communication transmitter of the circuitry, wherein the processor is configured to execute the program instructions.

9. The system of claim 1, wherein the EEG device comprises the processor and the memory including the program instructions stored in the memory, wherein the processor is configured to execute the program instructions.

10. The system of claim 1, further comprising:
    the controllable device and a controller coupled to or in communication with the controllable device and the processor, configured to control the premises related service provided by the controllable device in the area, in response to the control data signal in a real time operational phase.

11. The system of claim 1, wherein execution of the program instructions further configures the processor to:
    using the stored data, interpret later detection of additional EEG signals from a brain of the user, via the EEG device and the circuitry, to analyze the additional EEG signals to determine that the additional EEG signals correspond to the control instruction;
    generate the control data signal based on the control instruction;
    determine whether or not the control operation of the control data signal is consistent with the additional EEG signals based on another trusted input from the user; and
    upon determination that the control operation is not consistent with the additional EEG signals, modify the recognition data stored in the memory.

12. The system of claim 11, wherein function to modify the recognition data comprises modify the recognition data characterizing EEG signals as the predetermined set of signals in association with the control instruction, based on characterizing data derived from the additional EEG signals.

13. The system of claim 11, wherein function to modify the recognition data comprises functions to:
   identify another control instruction; and
   store, as data in the memory, the recognition data characterizing the additional EEG signals as another predetermined set of signals, in association with the another control instruction.

14. The system of claim 1, further comprising:
   a neural device configured to be positioned on a part of a body of the user, wherein the neural device includes one or more nerve sensors configured to detect nerve signals from nerves in the part of the body of the user,
   wherein the circuitry is coupled to the one or more nerve sensors and further configured to process the detected nerve signals via the one or more sensors of the neural device; and
   wherein, in the training phase, execution of the program instructions further configures the processor to:
      determine whether or not the control operation of the control data signal is also consistent with the detected nerve signals based on another trusted input from the user, and
      upon determination that the control operation is also consistent with the detected nerve signals, store recognition data characterizing the detected nerve signals as another predetermined set of signals in association with the control instruction.

15. A system comprising:
   an electroencephalography (EEG) device configured to be positioned on a head of a user, wherein the EEG device includes one or more electrodes configured to detect signals from a brain of the user;
   circuitry coupled to the one or more electrodes configured to process signals detected via the one or more electrodes of the EEG device;
   a processor coupled to or in communication with the circuitry;
   a memory accessible by the processor;
   program instructions stored in the memory for execution by the processor;
   data stored in the memory comprising a control instruction,
   wherein execution of the program instructions configures the processor to:
   generate, based on the control instruction, a control data signal, for control of an operation of a controllable device configured to provide a premises related service in an area of a premises; and
   wherein, in a training phase, execution of the program instructions further configures the processor to:
      determine whether or not that the control operation of the control data signal is consistent with the detected EEG signals based on a trusted input from the user,
      upon determination that the control operation is not consistent with the detected signals, associate the detected EEG signals with another control instruction in the data, wherein the another control instruction is different from the control instruction,
      determine that the association is consistent with the another control instruction based on another trusted input from the user, and
      store, in a memory, recognition data characterizing the detected EEG signals as a predetermined set of signals in association with the another control instruction.

16. The system of claim 15, wherein the execution of the program instructions configures the processor to associate the detected EEG signals with the another control instruction in the data.

17. The system of claim 15, wherein execution of the program instructions configures the processor to:
   generate, based on the another control instruction, another control data signal, for control of the operation of a controllable device configured to provide a premises related service in an area of a premises.

18. The system of claim 15, further comprising: the controllable device and
   a controller coupled to or in communication with the controllable device and the processor,
   configured to control the premises related service provided by the controllable device in the area, in response to the another control data signal in a real time operational phase.

19. The system of claim 15, further comprising:
   a neural device configured to be positioned on a part of a body of the user, wherein the neural device includes one or more nerve sensors configured to detect nerve signals from nerves in the part of the body of the user,
   wherein the circuitry is coupled to the one or more nerve sensors and further configured to process the detected nerve signals via the one or more sensors of the neural device; and
   wherein, in the training phase, execution of the program instructions further configures the processor to:
      determine whether or not the control operation of the control data signal is also consistent with the detected nerve signals based on a first trusted input from the user,
      upon determination that the control operation is also not consistent with the detected nerve signals, associate the detected nerve signals with a first control instruction in the data, wherein the first control instruction is different from the control instruction,
      determine that the association is consistent with the first control instruction based on a second trusted input from the user, and
      store recognition data characterizing the detected nerve signals as a predetermined set of signals in association with the first control instruction.

* * * * *